United States Patent
Vuong et al.

(10) Patent No.: US 10,247,724 B1
(45) Date of Patent: Apr. 2, 2019

(54) OPTICALLY CLEAR SEALABLE PETRI DISH BIOREACTOR

(71) Applicant: Autobiologic Inc., Santa Ana, CA (US)

(72) Inventors: An Vuong, Santa Ana, CA (US); Charlie Chandsawangbhuwana, Irvine, CA (US)

(73) Assignee: Autobiologic Inc., Santa Ana, CA (US)

( * ) Notice: Subject to any disclaimer, the term of this patent is extended or adjusted under 35 U.S.C. 154(b) by 0 days.

(21) Appl. No.: 15/972,002

(22) Filed: May 4, 2018

Related U.S. Application Data

(60) Provisional application No. 62/564,395, filed on Sep. 28, 2017.

(51) Int. Cl.
    *C12M 3/00* (2006.01)
    *C12M 1/00* (2006.01)
    *G01N 33/50* (2006.01)
    *C12M 1/32* (2006.01)

(52) U.S. Cl.
    CPC ......... *G01N 33/5085* (2013.01); *C12M 21/08* (2013.01); *C12M 47/04* (2013.01); *G01N 33/5091* (2013.01); *C12M 23/12* (2013.01); *C12M 23/40* (2013.01)

(58) Field of Classification Search
    CPC ...... C12M 23/42; C12M 23/48; C12M 33/04; C12M 23/04; C12M 23/10
    See application file for complete search history.

(56) References Cited

U.S. PATENT DOCUMENTS

| | | | |
|---|---|---|---|
| 2,942,520 A | 6/1960 | Rose | |
| 2,975,553 A | 3/1961 | John | |
| 3,055,808 A * | 9/1962 | Henderson | B65D 43/0214 435/305.3 |
| 4,033,825 A | 7/1977 | Haddad et al. | |
| 4,090,921 A | 5/1978 | Sawamura et al. | |
| 4,154,652 A | 5/1979 | Sawamura et al. | |
| 4,299,921 A | 11/1981 | Youssef | |
| 4,435,508 A | 3/1984 | Gabridge et al. | |
| 4,800,164 A | 1/1989 | Bisconte et al. | |

(Continued)

FOREIGN PATENT DOCUMENTS

EP      1756262      12/2013

OTHER PUBLICATIONS

"A Bioreactor System for Clinically Relevant Bone Tissue Engineering", Frank Janssen, PhD Thesis, University of Twente, Enschede, The Netherlands, 2010 (174 pages).

(Continued)

*Primary Examiner* — Nathan A Bowers
(74) *Attorney, Agent, or Firm* — Knobbe, Martens, Olson & Bear, LLP

(57) ABSTRACT

A Petri dish bioreactor can allow a standard Petri dish to be converted to a microscopically observable bioreactor. A bioreactor can be formed by the compression of a device against the edge of a Petri dish thus creating a sealed isolated chamber. One advantage of this conversion is to provide an inexpensive device that can be used for cell culture, observation, transportation, and storage in the laboratory and clinical setting. Further, by creating a sealed bioreactor chamber accessible by ports, the device can reduce cross contamination and allow for the maintenance of a controlled microenvironment within the bioreactor.

26 Claims, 40 Drawing Sheets

(56) References Cited

U.S. PATENT DOCUMENTS

| | | | |
|---|---|---|---|
| 5,181,382 | A | 1/1993 | Middlebrook |
| 5,190,878 | A | 3/1993 | Wilhelm |
| 5,424,209 | A | 6/1995 | Kearney |
| 5,571,721 | A * | 11/1996 | Turner .................. B01L 3/5085 359/398 |
| 5,612,188 | A | 3/1997 | Shuler et al. |
| 5,985,653 | A | 11/1999 | Armstrong et al. |
| 5,994,129 | A | 11/1999 | Armstrong et al. |
| 6,008,010 | A | 12/1999 | Greenberger et al. |
| 6,048,721 | A | 4/2000 | Armstrong et al. |
| 6,197,575 | B1 | 3/2001 | Griffith et al. |
| 6,228,635 | B1 | 5/2001 | Armstrong et al. |
| 6,238,908 | B1 | 5/2001 | Armstrong et al. |
| 6,521,451 | B2 | 2/2003 | Potter |
| 6,534,014 | B1 * | 3/2003 | Mainquist ........... B01L 3/50853 422/551 |
| 6,569,675 | B2 * | 5/2003 | Wall ...................... C12M 23/08 435/294.1 |
| 6,670,170 | B1 | 12/2003 | Gaffin et al. |
| 7,635,586 | B2 | 12/2009 | West |
| 8,110,394 | B2 | 2/2012 | Hasegawa et al. |
| 8,216,831 | B2 | 7/2012 | Kobayashi et al. |
| 8,294,757 | B2 | 10/2012 | Yu et al. |
| 8,372,358 | B2 | 2/2013 | Groisman et al. |
| 8,383,397 | B2 | 2/2013 | Wojciechowski et al. |
| 8,492,140 | B2 | 7/2013 | Smith et al. |
| 8,507,266 | B2 | 8/2013 | Welter et al. |
| 8,546,142 | B2 | 10/2013 | Martin et al. |
| 9,206,383 | B2 | 12/2015 | Vunjak-Novakovic et al. |
| 9,226,494 | B2 | 1/2016 | Chang et al. |
| 9,499,780 | B2 | 11/2016 | Smith et al. |
| 9,575,055 | B2 | 2/2017 | Gevaert et al. |
| 2003/0113905 | A1 * | 6/2003 | Ho ........................ C12M 41/12 435/287.1 |
| 2005/0130297 | A1 * | 6/2005 | Sarem .................... C12M 23/12 435/297.1 |
| 2005/0260742 | A1 * | 11/2005 | Watanabe .................. B01L 9/52 435/287.3 |
| 2005/0282268 | A1 | 12/2005 | Kagayama et al. |
| 2006/0050376 | A1 | 3/2006 | Houston et al. |
| 2007/0081419 | A1 | 4/2007 | Mou |
| 2008/0064090 | A1 * | 3/2008 | Whittlinger ........... B01L 3/5085 435/305.3 |
| 2009/0141345 | A1 * | 6/2009 | Tsuchiya ................ B01L 9/523 359/393 |
| 2013/0210130 | A1 | 8/2013 | Larcher et al. |
| 2014/0087410 | A1 * | 3/2014 | Tanaka .................... C12Q 1/02 435/29 |
| 2015/0191687 | A1 | 7/2015 | Jung et al. |
| 2015/0218503 | A1 * | 8/2015 | Kiyama .................. C12M 23/10 435/297.1 |
| 2016/0152936 | A1 | 6/2016 | Bargh et al. |
| 2016/0201037 | A1 | 7/2016 | Tuan et al. |
| 2016/0264918 | A1 | 9/2016 | Shimase et al. |
| 2016/0326476 | A1 | 11/2016 | Maisch et al. |
| 2016/0369224 | A1 | 12/2016 | Shimasaki et al. |
| 2017/0022468 | A1 | 1/2017 | Cesarini et al. |
| 2017/0096627 | A1 | 4/2017 | Smith et al. |

OTHER PUBLICATIONS

"A Continuous-Flow Method of Organ Culture", McAteer, et al., In Vitro, vol. 14, No. 9, 1978 (9 pages).

"A Novel Flow Perfusion Bioreactor Supports 3d Dynamic Cell Culture", Alexander M. Sailon, et al., Journal of Biomedicine and Biotechnology, vol. 2009, Article ID 873816, 2009 (8 pages).

"Bioreactor Systems for Bone Tissue Engineering", Juliane Rauh, Ph.D., et al., Tissue Engineering: Part B, vol. 17, No. 2, 2011 (19 pages).

"Bioreactors for Bone Tissue Engineering", A J El Haj, et al., Institute for Science and Technology in Medicine, Keele University, Thornburrow Drive, Hartshill, Stoke-on-Trent, UK 2010 (11 pages).

"Bioreactors in Tissue Engineering", S. Partap et al, Department of Anatomy, Royal College of Surgeons in Ireland, Trinity Centre for Bioengineering, Department of Mechanical Engineering, Dublin, Ireland, 2010 (15 pages).

"Bone Tissue Engineering Bioreactors: Dynamic Culture and the Influence of Shear Stress", Andrew B. Yeatts, et al., Elsevier Journal, 2011 (11 pages).

"Culture Dish Perfusion With Cinemicrography", LaRoy N. Castor, Tissue Culture: Methods and Applications, pp. 298-303, Academic Press, Elsevier, Inc. (1973).

"Design and Functional Testing of a Multichamber Perfusion Platform for Three-Dimensional Scaffolds", Marco Piola, et al., The Scientific World Journal, vol. 2013, Article ID 123974, 2013 (10 pages).

"Design and Use of Multiplexed Chemostat Arrays", Aaron W. Miller, et al., Jove Journal of Visualized Experiments, 2013 (6 pages).

"Design and Validation of a Dynamic Flow Perfusion Bioreactor for Use With Compliant Tissue Engineering Scaffolds", Michael J. Jaasma, et all, Elsevier, Journal of Biotechnology 133, 2008 (7 pages).

"Design of a Flow Perfusion Bioreactor System for Bone Tissue-Engineering Applications", Gregory N. Bancroft, et al., Tissue Engineering, vol. 9, No. 3, 2003 (6 pages).

"Ectopic Bone Formation in Collagen Sponge Self-Assembled Peptide-Amphiphile Nanofibers Hybrid Scaffold in a Perfusion Culture Bioreactor", Hossein Hosseinkhani, et al., Elsevier, Biomaterials 27, 2006 (10 pages).

"Effects of Initial Seeding Density and Fluid Perfusion Rate on Formation of Tissue-Engineered Bone", Warren L. Grayson, Ph.D., et al., NIH Author Manuscript, 2008 (19 pages).

"Effects of Medium Perfusion Rate on Cell-Seeded Three Dimensional Bone Constructs in Vitro", Sarah H. Cartmell, et al., Tissue Engineering, vol. 9, No. 6, 2003 (7 pages).

"Engineering Anatomically Shaped Human Bone Grafts", Warren L. Grayson et al., PNAS, vol. 107, No. 8, 2010 (6 pages).

Petri Dish Insert Manual, www.biosciencetools.com (Dec. 3, 2016).

"The Circumfusion System for Multipurpose Culture Chambers", George G. Rose, The Journal of Cell Biology, vol. 32, 1967 (24 pages).

"The Role of Bioreactors in Tissue Engineering for Musculoskeletal Applications", Emeka Oragui, et al., The Open Orthopaedics Journal, 2011, 5, 2011 (4 pages).

"The Role of Perfusion Bioreactors in Bone Tissue Engineering", Diana Alves Gaspar et al, Biomatter, 2:4, 167-175 2012 (10 pages).

* cited by examiner

OPTICALLY CLEAR SEALABLE PETRI DISH BIOREACTOR

INCORPORATION BY REFERENCE TO ANY PRIORITY APPLICATIONS

This application claims the benefit under 35 U.S.C. § 119(e) as a nonprovisional application of U.S. Prov. App. No. 62/564,395 filed on Sep. 28, 2017, which is hereby incorporated by reference in its entirety. Any and all applications for which a foreign or domestic priority claim is identified in the Application Data Sheet as filed with the present application, as well as applications mentioned in the specification are hereby incorporated by reference under 37 CFR 1.57.

BACKGROUND

Field of the Invention

This invention relates in some aspects to a biomedical device utilized to cultivate and microscopically examine microorganisms and cells.

Description of the Related Art

Bioreactors are primarily used for cell culture where they are used to cultivate bacteria, yeast, and animal cells for the basic science, biotechnology, pharmaceutical, and medical industries. Small scale bioreactors are often used for cell expansion and conditioning for tissue engineering but they can also be used to model healthy or pathological tissue for basic science research, drug testing, and drug development. Larger industrial scale bioreactors are frequently used for biological drug production. All bioreactors can be characterized as having a sealed controlled environment that contains the cells of interest. They may have resealable ports to infuse solutions, withdraw samples, and to insert probes for monitoring media chemistry such as pH and conditions such as temperature. Some incorporate an area that can view the cells microscopically. Bioreactors preferably maintain an isolated and stable microenvironment for the biological sample to support uncontaminated and controlled growth.

Currently, to the inventors' knowledge there are no commercially available products that create a sealable watertight bioreactor using a Petri dish and bioreactor adapter. Thus there is a need for a product that converts the ubiquitous Petri dish into a bioreactor device.

SUMMARY

The invention can include in some embodiments a device which can adapt to a standard Petri dish to convert it to a bioreactor, and/or an integrated Petri dish bioreactor in some embodiments.

Most commercially available bioreactors are for industrial use and are extremely costly. The large scale of these devices may also be inappropriate for research and for personalized medicine applications. In addition, the cells in these bioreactors cannot be observed microscopically without withdrawing a sample. Smaller bioreactors used for research that attach to standard culture plates, e.g., Petri dishes, are not watertight and airtight. When perfusing new media into a Petri dish with a perfusion pump, there can be a problem of perfusion mismatch which can cause overflow and increase the risk for environmental contamination. Ensuring sterility is another challenge since the components used in these designs are often not sterile single-use. Biofilm accumulation on bioreactor components can be a source of contamination and can be a concern when resterilizing. In a microbiology application, growing anaerobic bacteria is also not possible in many of these systems because they are not airtight.

A culture plate, e.g., Petri dish bioreactor adapter, henceforth known as an "adapter," can in some embodiments be a device that can be used to convert, for example, a commercial off-the-shelf Petri dish into a microscopically observable bioreactor, henceforth known as a "Petri dish bioreactor."

The adapter can include two or more components, a Petri dish bioreactor adapter body, henceforth known as an "adapter body," and a Petri dish bioreactor adapter compression cap, henceforth known as an "adapter compression cap". A sealed bioreactor compartment can be created using an adapter compression cap that compresses the Petri dish against the adapter body. In some embodiments, the Petri dish is integrally formed as part of the bioreactor system. The adapter compression cap can be threaded or has a push fitting to mate with the adapter body. The adapter compression cap also can have a window that allows the bottom of the Petri dish to be viewed microscopically from below. Watertightness can be achieved with the Petri dish compressing against a seated adapter body gasket or a compressible portion of the adapter body. In another version the adapter compression cap conforms to the gasketless adapter body to create a watertight seal.

The adapter body can also have an area called the "light transmission window" to allow light such as visible, UV, and/or infrared light for example to pass through the Petri dish bioreactor and onto a microscope objective to allow for microscopic viewing of cells. The adapter body can include one, two, or more ports that are designed to accept, e.g., male or female Luer connections on sterile single use tubing that are commonly used in the biomedical field. These ports can be used for, monitoring, media perfusion, drug administration and/or sampling. Sterile commercially available air filters can be attached to these ports to simulate aerobic and microaerophilic environments. Further, port caps placed on the ports can be used to simulate an anaerobic environment in the Petri dish bioreactor chamber after purging the air gap with a gas such as nitrogen.

Some embodiments of Petri dish bioreactors can allow for increased efficiency with a reduction of production cost for cell culture. The customizable ports of the adapter body allow for flexibility in choosing various types of tubing, connections, filters, and port caps for different applications. Readily available Petri dishes are inexpensive and can be discarded after use. The adapter body and the adapter compression cap can also be disposable, but in some embodiments can be made from a resterilizable material to reduce cost. From an infection control standpoint, the device can advantageously reduce cross contamination in the laboratory or clinical setting. The device allows for cells to be observed, manipulated, transported, and stored safely.

Some embodiments of Petri dish bioreactors can include any number of the following elements. A Petri dish can be coupled to an adapter body using an adapter compression cap to create an bioreactor system. The adapter body and adapter compression cap can be made from material such as, for example, polysulfone for autoclavable embodiments and PCTG for disposable embodiments. The bioreactor can include an optically clear material to support microscopic viewing, can be mechanically strong to support the compression mechanism, have similar thermal expansion coefficients to prevent loosening of components, and biocompatible to support biological growth.

In some embodiments, the adapter body can include one, two, or more shallow angle 15 to 65 degrees flow ports capable of allowing perfusion through a chamber, permitting direct pipette access to the bottom of the Petri dish, not obscuring the central microscopic viewing area, allowing for a thinner profile for short working distance microscope condensers, and/or preventing spillage at the port openings. The adapter body can also include a gasket with a concave central groove that accommodates the lip of the Petri dish to allow for precise and easy fitting and alignment of the Petri dish to the adapter body when compressed together using the adapter compression cap.

The adapter compression cap can include an internal thread that connects to the adapter body that includes an external thread. The adapter compression cap can include a moat surrounding the Petri dish designed to hold spillage from the Petri dish. The compression cap can allow for a snap friction fit of the Petri dish to allow for easy handling that reduces sample cross-contamination. The compression cap can also be a separate component, or integrated with the Petri dish as a single component.

In some embodiments, Petri dish bioreactor can include an adapter body. The adapter body can include a baffle, and the baffle can include at least one barrier wall to alter natural flow within the bioreactor.

Some embodiments of Petri dish bioreactors can include adapter body ports. The adapter body port can allow direct coupling to male Luer, female Luer, Luer locking, barbed, or threaded fittings. In some embodiments, an insertable or integrated baffle can be placed into the bioreactor to direct flow. A fluid handling system including any number of reservoirs, pumps, fittings, and/or tubings can be connected to the inlet and outlet ports to provide automated perfusion. The adapter body port can be processed, wherein the fluid exiting the outlet ports can be filtered and returned to the bioreactor via the inlet ports, and wherein the bioreactor can be linked to a single waste outlet.

In some embodiments, the adapter body port can be operatively connected independent sensors. The independent sensors can monitor environmental conditions such as pH, temperature, oxygen concentration, dissolved oxygen, and/or flow rate. The sensors can be located upstream of the bioreactor to measure media conditions. The sensors in the bioreactor can measure extracellular conditions. The sensors can be located downstream of the bioreactor to measure cellular waste conditions.

In some embodiments, environment of the bioreactor can be controlled. In some embodiments, the internal temperature of the bioreactor can be controlled by heaters and a controller system. In some embodiments, the extracellular pH of the bioreactor can be controlled using a chemical buffer such as HEPES (4-(2-hydroxyethyl)-1-piperazineethanesulfonic acid) and/or MOPS (3-(N-morpholino) propanesulfonic acid). In some embodiments, the internal bioreactor pH can be controlled using a bicarbonate buffer with a set atmospheric carbon dioxide level. The internal bioreactor pH can be controlled using a bicarbonate buffer with a media carbonator.

In some embodiments, cells loaded into the bioreactor can be imaged. The Petri dish can be modified to have a glass bottom, and the adapter body can be made of an optically clear material. The adapter compression cap can allow light through the center of the Petri dish. In some embodiments, the bioreactor can be monitored by one or more cameras. In some embodiments, the bioreactor can be coupled to any number of its own microscope and camera. Some embodiments of Petri dish bioreactor can include any number of bioreactors operatively linked together and/or are mounted onto one or more removable storage carriers In some embodiments, the bioreactors can be autoclavable. In some embodiments, the storage carriers can be autoclavable.

In some embodiments, the Petri dish bioreactor can be used for biomedical purposes. Cells can be cultured to assess bacterial infection and/or to assess drug effectiveness. Biopsy can be cultured and the malignancy of a tumor can be assessed. In some embodiments, biopsies of diseased and healthy tissues can be cultured and the effectiveness and toxicity of chemotherapy or radiation treatments can be evaluated. In some embodiments, healthy patient-derived tissue can be grown for use in reconstructive surgery to replace surgically removed tissue. The patient-derived tissue can also be grown for general implantation surgery.

In some embodiments, an isolated bioreactor system for creating a watertight and airtight seal between the bioreactor and a surrounding environment can include any number of the following elements. The system can include an adaptor compression cap, an adaptor body, and/or a gasket. The adapter compression cap can be operatively connected to a petri dish to hold the petri dish in place. The adapter compression cap can further include a first connection component. The adapter body can include any number of the following elements. The adaptor body can include a transmission window, at least one port, and a second connection component. The transmission window can allow transmission of light through a top surface of the adaptor body to the petri dish. The at least one port can be connected to the adapter body at an angle with respect to a horizontal axis defined by a bottom surface of the petri dish. The angle of the at least one port can be between about 15 degrees and about 65 degrees. The second connection component can interacts with the first component to generate compression between the adapter body and the adapter compression cap. The gasket can operatively connect to the adaptor body and the petri dish of the bioreactor system.

In some embodiments, the bioreactor system can include at least two input ports. In some embodiments, the input ports are angled with respect to a horizontal axis of an inferior surface of the culture plate. The angle of the input ports can be between about 15 degrees and about 65 degrees. In some embodiments, the input ports can be hingedly connected to the adapter body and the angle can be adjusted between about 15 degrees and about 65 degrees. In some embodiments, the first connection element of the adaptor compression cap and the second connection component of the adaptor body can include complementary threaded surfaces. In some embodiments, the gasket can include at least one arcuate concave groove that, when compressed against the petri dish, can interact with a wall of the petri dish. In some embodiments, the bioreactor system can further include an output port and an environment sensor. The environment sensor can be in communication with the output port. In some embodiments, the at least one input port can be operably connected to a fluid or gas pump. In some embodiments, the adaptor body can include a baffle. In some embodiments, the baffle can include at least one barrier wall to alter natural flow within the bioreactor.

In some embodiments, a bioreactor system with an enhanced seal can include any number of the following elements. The bioreactor system can include a culture plate that can include a sidewall, a closed inferior end, and an open superior end. The bioreactor system can include a first adapter component. The first adapter component can include a central aperture configured to house the culture plate therein. The adapter component can further include an inner ring configured to contact the sidewall of the culture plate, and an outer ring. The outer ring can include a reversible locking element. The bioreactor system can include an arcuate gasket. In some embodiments, the arcuate gasket can include a superior-facing surface and an inferior-facing surface. The inferior-facing surface can include a preformed concave groove configured to mate with the sidewall of the culture plate within the groove. The bioreactor system can include a second adapter component. In some embodiments, the second adapter component can include a reversible locking element, at least one input port, and/or a circumferential groove configured to house the arcuate gasket therein. The bioreactor system can be reversibly transformable from an unlocked configuration to a locked configuration, such that an airtight seal within the culture plate can be created in the locked configuration.

In some embodiments, the second adapter component can include at least one laterally-extending tab. In some embodiments, the at least one input port of the second adapter component can be angled with respect to a horizontal axis of an inferior surface of the culture plate. The angle of the at least one input port of the second adapter component can be between about 15 degrees and about 65 degrees. In some embodiments, the bioreactor system can include at least one baffle configured to separate adjacent zones of the culture plate. The at least one baffle can be configured to fit within a slot of the second adapter component. In some embodiments, the reversible locking element of the first adapter component and the second adapter component can include complementary threaded surfaces. In some embodiments, the culture plate can be removably attached to the first adapter component. In some embodiments, the culture plate can be integrally formed with the first adapter component. In some embodiments, the gasket can include a flexible material. In some embodiments, the superior-facing surface of the arcuate gasket can include a concave surface.

DETAILED DESCRIPTION

Various embodiments of a culture plate, e.g., Petri dish, bioreactor 100 are described herein below. In some embodiments, the Petri dish bioreactor 100 is created by coupling a culture plate (or the bottom half thereof), e.g., Petri dish 1 to an adapter body 2 using an adapter compression cap 4. The adapter compression cap 4 and the adapter body 2 can be fastened together to create a watertight and airtight seal between an environment inside and outside the Petri dish bioreactor 100.

Figure 1:
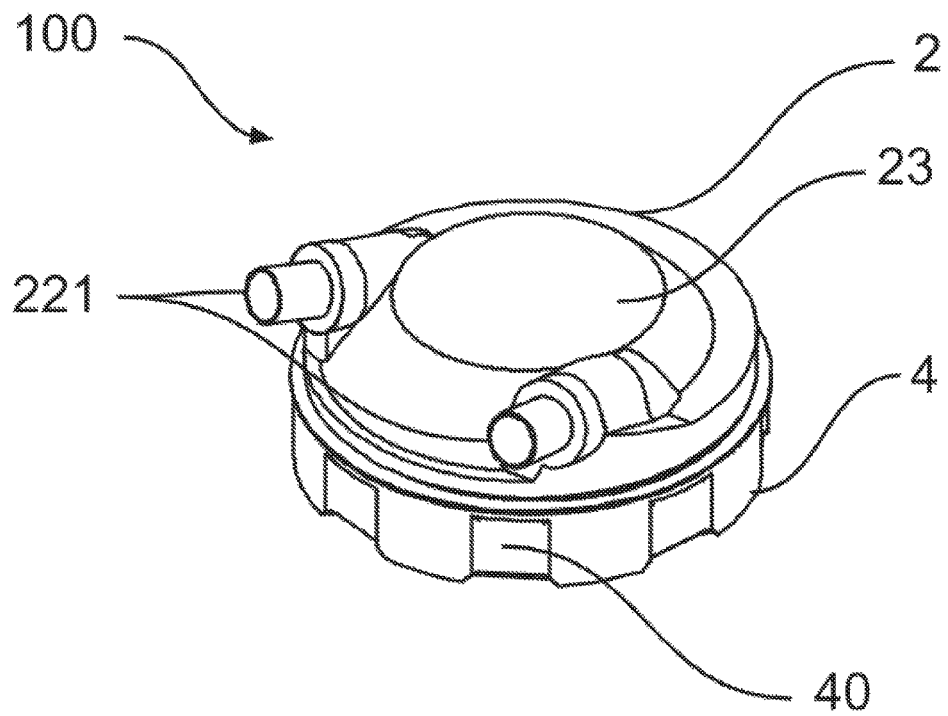
FIG. 1 is a schematic of an embodiment of the present invention assembled with two female Luer perfusion ports and a screw-on adapter compression cap.

FIG. 1 is a schematic of an embodiment of a Petri dish bioreactor 100 assembled. The Petri dish bioreactor 100 includes an adapter body 2 and an adapter compression cap 4. The adapter body 2 and adapter compression cap 4 can be made from material such as, for example, polysulfone for autoclavable embodiments and PCTG for disposable embodiments. The bioreactor 100 can include an optically clear material to support microscopic viewing, can be mechanically strong to support the compression mechanism, have similar thermal expansion coefficients to prevent loosening of components, and biocompatible to support biological growth. In some embodiments, the adapter body 2 has a light transmission window 23 and a plurality of ports, which can be, for example, Luer angled ports 221 (e.g., female Luer perfusion ports). In some embodiments, the adapter compression cap 4 has grip indentations 40 spaced regularly apart as shown. In some embodiments, the grip indentations 40 may not be spaced regularly. In some embodiments, indented areas for the grip indentations 40 may be made in different materials to assist in holding and/or turning the adapter compression cap 4. The adapter body 2 can include a light transmission window 23 on its top surface. The light transmission window 23, in some embodiments, can be made with the same material as the adapter body 2 and/or the adapter compression cap 4. In some other embodiments, the light transmission window 23 is made of a different material than the adapter compression cap 4 and/or the adapter body 2.

Figure 2:
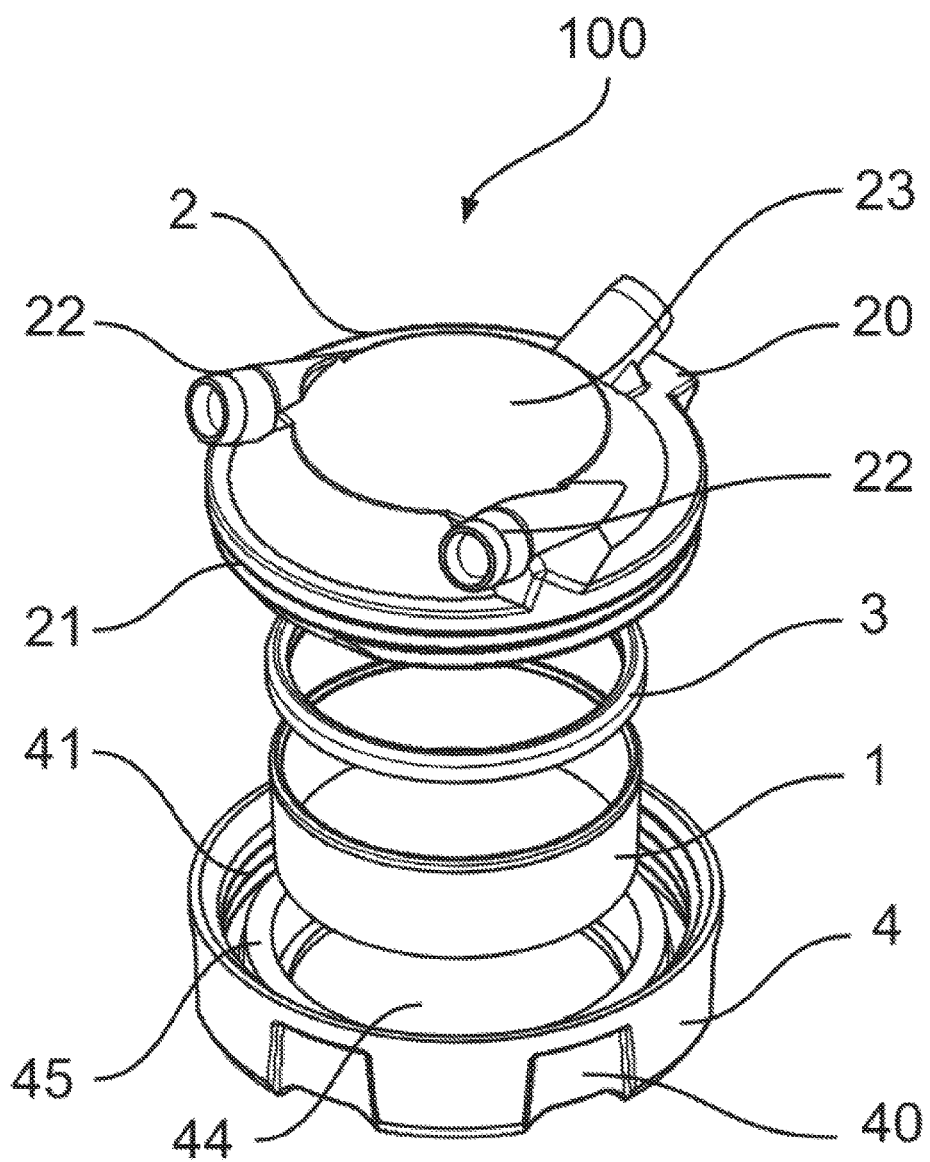
FIG. 2 is an exploded view of an embodiment of the present invention that allows for microscope viewing. The adapter compression cap contains a hole and holds the Petri dish edge. The adapter body is optically transparent.

FIG. 2 shows an exploded view of the Petri dish bioreactor 100 illustrated in FIG. 1. In some embodiments, the Petri dish bioreactor 100 includes a Petri dish 1, the adapter body 2, the adapter compression cap 4, and a gasket 3.

The adapter compression cap 4 can have grip indentations 40, compression cap thread 41, a Petri dish slot 44, and/or a Petri dish ridge 45. The grip indentations 40 provide an operator with an enhanced grip for the Petri dish bioreactor 100 and the adapter compression cap 4. The Petri dish ridge 45 defines the Petri dish slot 44 of the adapter compression cap 4. For example, the Petri dish ridge 45 circumferentially defines the Petri dish slot 44 so that the Petri dish 1 may be placed within the Petri dish slot 44. In some embodiments, the Petri dish ridge 45 envelops the entire Petri dish 1. In some embodiments, the Petri dish ridge 45 envelops at least a portion of the Petri dish 1. The Petri dish ridge 45 may be made out of the same material used for the adapter compression cap 4. In some embodiments, the Petri dish ridge 45 is made out of a different material than material used for the adapter compression cap 4. The material used for the Petri dish ridge 45 can be flexible and/or absorbent. An absorbent Petri dish ridge 45 can absorb any spills from the Petri dish 1 and a flexible Petri dish ridge 45 can assist the operator in placing the Petri dish 1 within the Petri dish slot 44 with more ease.

The adapter body 2 has an indexing extrusion 20, at least one angled ports 22, adapter body thread 21, and/or a light transmission window 23. The indexing extrusion 20 allows indexing of the Petri dish bioreactor 100 as will be discussed in a later section of the description. The angled ports 22 operatively connected to the adapter body 2 at an angle provide an access to the Petri dish bioreactor 100. The adapter body thread 21 interacts with the compression cap thread 41 to operatively connect the adapter body 2 and the adapter compression cap 4. In some embodiments, the compression cap thread 41 is an external thread facing radially outward from the center of the adapter body 2. In some embodiments, the compression cap thread 41 is an internal thread facing radially inward towards the center of the adapter compression cap 4. However, it should be noted that the adapter body thread 21 and the compression cap thread 41 can be oriented in a way to provide a watertight and airtight seal between the adapter body 2 and the adapter compression cap 4.

In some embodiments, the adapter body 2 includes a light transmission window 23 that allows for microscopic viewing. The light transmission window 23 may be located on the top surface of the adapter body 2. The light transmission window 23 allows passage of light from an imaging element (e.g., microscope condenser) through the Petri dish bioreactor 100 to a microscope objective. In some embodiments, the light transmission window 23 of the adapter body 2 is optically clear to allow optimal light transmission. Some embodiments include the light transmission window 23 that allows selective passage of light of a certain wavelength or frequency or range thereof. In some embodiments, the light transmission window 23 is configured to provide enlarged view of the sample inside the Petri dish bioreactor 100. Such configuration of the light transmission window 23 may incorporate a convex surface. In some embodiments, the light transmission window 23 incorporates at least one concave surface and at least one convex surface.

The Petri dish 1 can be in a substantially cylindrical shape as shown or other geometries, and has an open top as shown to receive culture media, reagents, and/or biologic sample material, for example. The Petri dish 1 can in some cases be mounted inside the adapter compression cap 4 so that the Petri dish 1 is located within an inner circumference of the Petri dish ridge 45 of the adapter compression cap 4. The Petri dish 1, in some embodiments, can have external or internal thread near the top of its arcuate wall and can be integrally incorporated to the adapter compression cap 4.

The gasket 3 can be placed between the adapter body 2 and the Petri dish 1. When the adapter compression cap 4 is compressed against the adapter body 2, the gasket 3 is compressed between the Petri dish 1 and the adapter body 2, creating a watertight and airtight seal. This seal prevents debris from entering into the Petri dish bioreactor 100, creating a closed environment within the bioreactor. In some embodiments, the Petri dish 1 may be fixedly mounted inside the adapter compression cap 4 within the Petri dish ridge 45 to prevent the Petri dish 1 from moving. As illustrated, the Petri dish ridge 45 can be configured to house the Petri dish 1 within, wherein the Petri dish ridge 45 is radially spaced apart from an outer ring of the adapter compression cap 4 incorporating the compression cap thread 41. The Petri dish ridge 45 can in some embodiments have a smooth non-threaded inner peripheral surface, while the outer ring of the adapter compression cap 4 can have a threaded inner peripheral edge and a non-threaded outer peripheral edge, the threads or locking features configured to mate with complementary threads or other reversible locking features of the adapter body 2, such as radially outer-facing peripheral edge of the adapter body 2. The threads can be on the opposite sides of the respective compression cap 4 and adapter body 2 in other embodiments.

Figure 3:
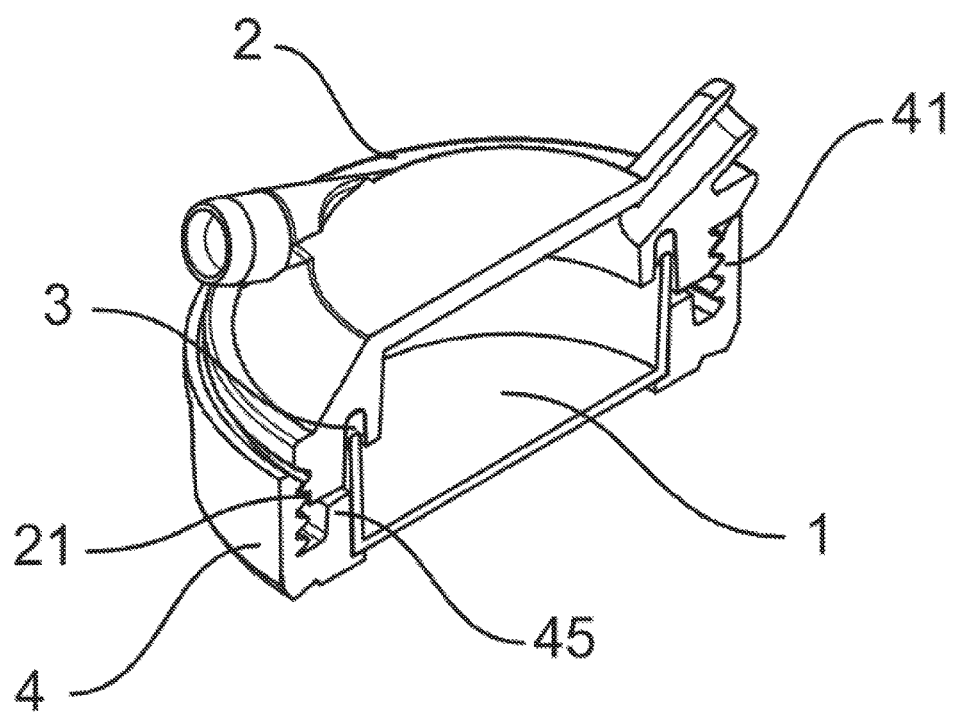
FIG. 3 is a cross-sectional view of an embodiment of the present invention showing the adapter compression cap threading.

FIG. 3 is a cross-sectional view of a Petri dish bioreactor 100. The Petri dish bioreactor 100 can include an adapter body 2, a gasket 3, and an adapter compression cap 4. One of the adapter body 2 and the adapter compression cap 4 can have a reversible locking element and the other can include a complementary locking element configured to interact with the reversible locking element. In some embodiments, the adapter compression cap 4 has an adapter compression cap thread 41 and associated complementary adapter body thread 21 of the adapter body 2. As explained above, the Petri dish 1 can be placed within an area inside the adapter compression cap 4 defined by a Petri dish ridge 45. The gasket 3 is placed between the Petri dish 1 and the adapter body 2 such that compression between the adapter compression cap 4 and the adapter body 2 via the adapter body thread 21 and the compression cap thread 41 creates a watertight and airtight seal for the Petri dish bioreactor 100.

The adapter compression cap 4 may be compressed against the adapter body 2 using various methods. As noted earlier, the adapter compression cap 4 and the adapter body 2 may have the compression cap thread 41 and the adapter body thread 21, respectively, that allow the compression cap 4 to be threaded into the adapter body 2 as previously described. In some embodiments, the adapter compression cap 4 and the adapter body 2 can be compressed against one another using a push fitting. In some embodiments, the adapter compression cap 4 and the adapter body 2 have at least one set of vertical and horizontal channels incorporated to their outer walls to allow an operator to push the adapter compression cap 4 and the adapter body 2 against one another and creating a seal between them by spinning one with respect to another.

Figure 4:
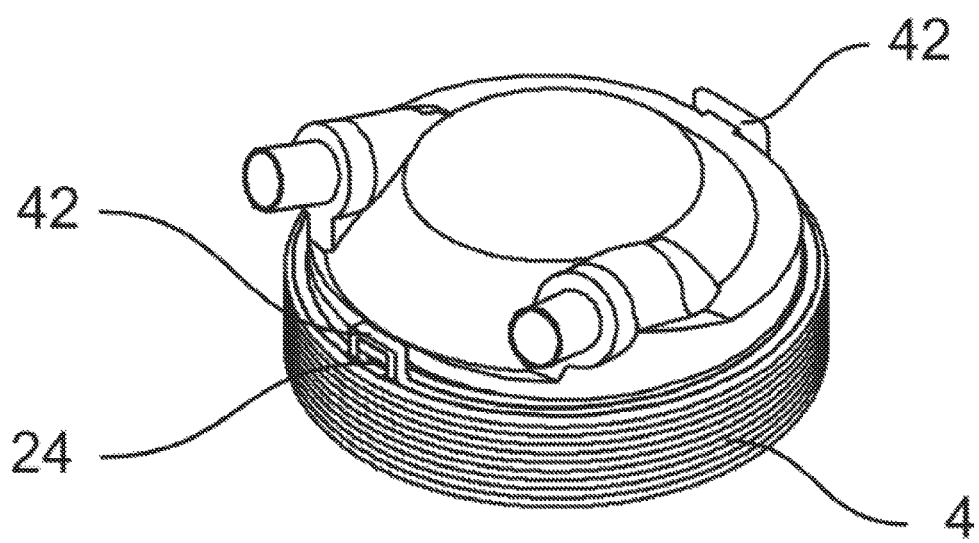
FIG. 4 is a schematic of an embodiment of the present invention assembled with push fitting adapter compression cap.
Figure 5:
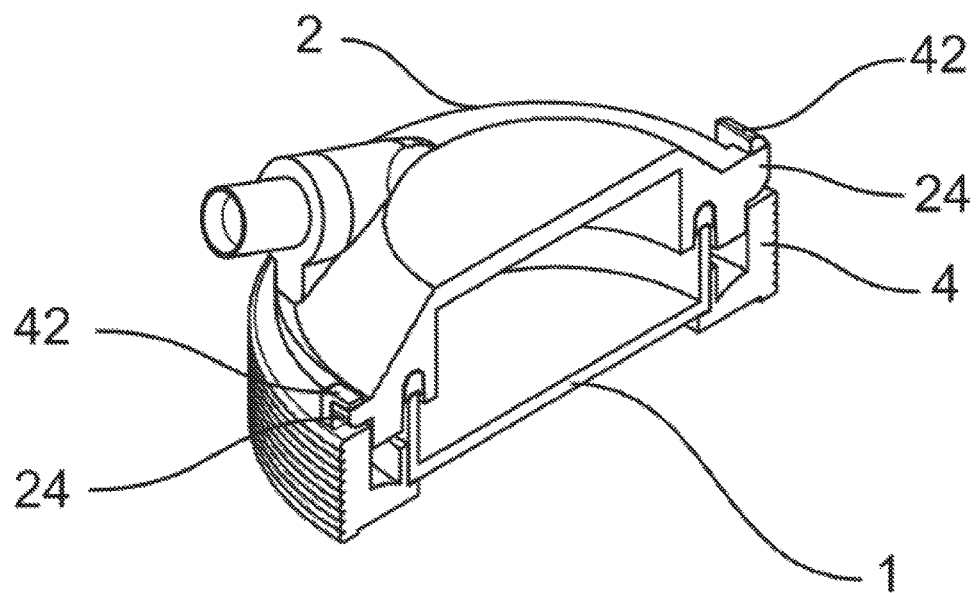
FIG. 5 is a cross-sectional view of an embodiment of the present invention with a push fitting adapter compression cap.

FIGS. 4 and 5 show the Petri dish bioreactor 100 including the adapter body 2 and the adapter compression cap 4, wherein the adapter body 2 and the adapter compression cap 4 are compressed against one another via a snap-on method. The adapter body 2 has one or more adapter body snap lock 24 and the adapter compression cap 4 has one or more corresponding compression cap snap lock 42. In some designs, the adapter body snap lock 24 may be flush with respect to an outer circumferential surface of the adapter body 2. In some other designs, the adapter body snap lock 24 may not be flush with respect to the outer circumferential surface of the adapter body 2 and instead protrude radially outward from the outer circumferential surface of the adapter body 2. The adapter body snap lock 24 interlocks with the adapter compression cap snap lock 42, thus maintaining compression between the adapter compression cap 4 and the adapter body 2. In the push fitting version, the adapter compression cap 4 incorporates a compression design to allow for easy push on installation of the adapter compression cap 4 to the adapter body 2. In some embodiments, the adapter compression cap 4 may be manufactured from a deforming plastic such as polyethylene or nylon to allow for the adapter compression cap 4 to conform onto and compress against both the undercut of the adapter body 2 and to also simultaneously compress the Petri dish 1 against the gasket 3.

Figure 6:
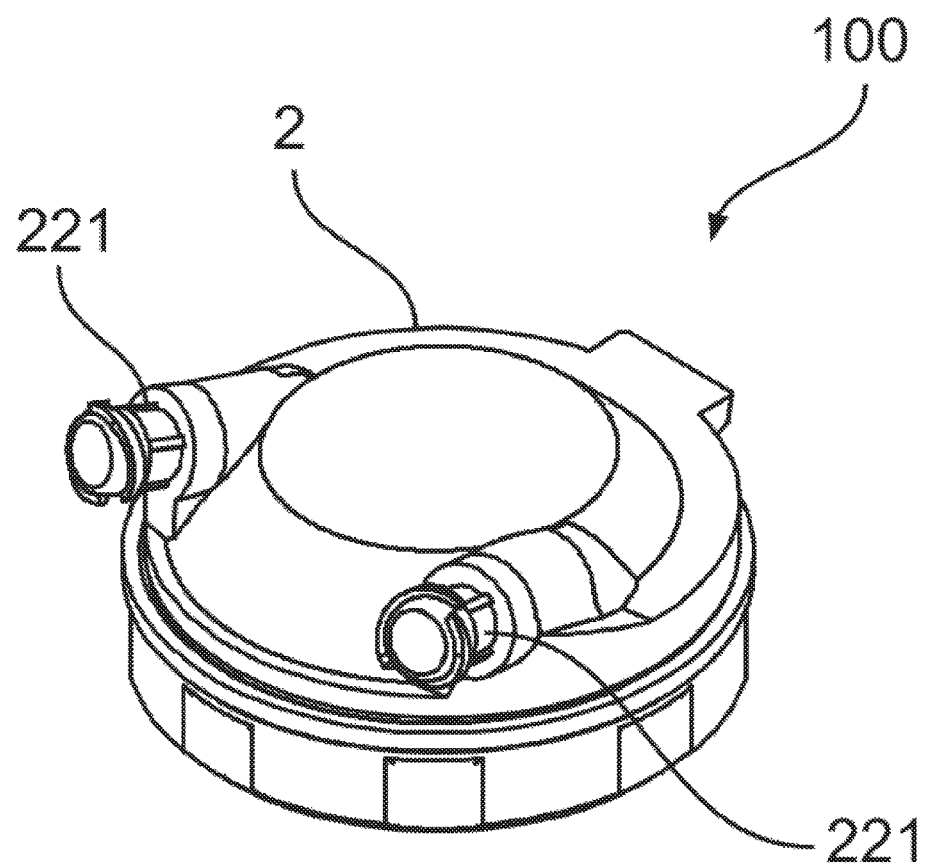
FIG. 6 is a schematic of an embodiment of the present invention having Luer locking perfusion ports.
Figure 7:
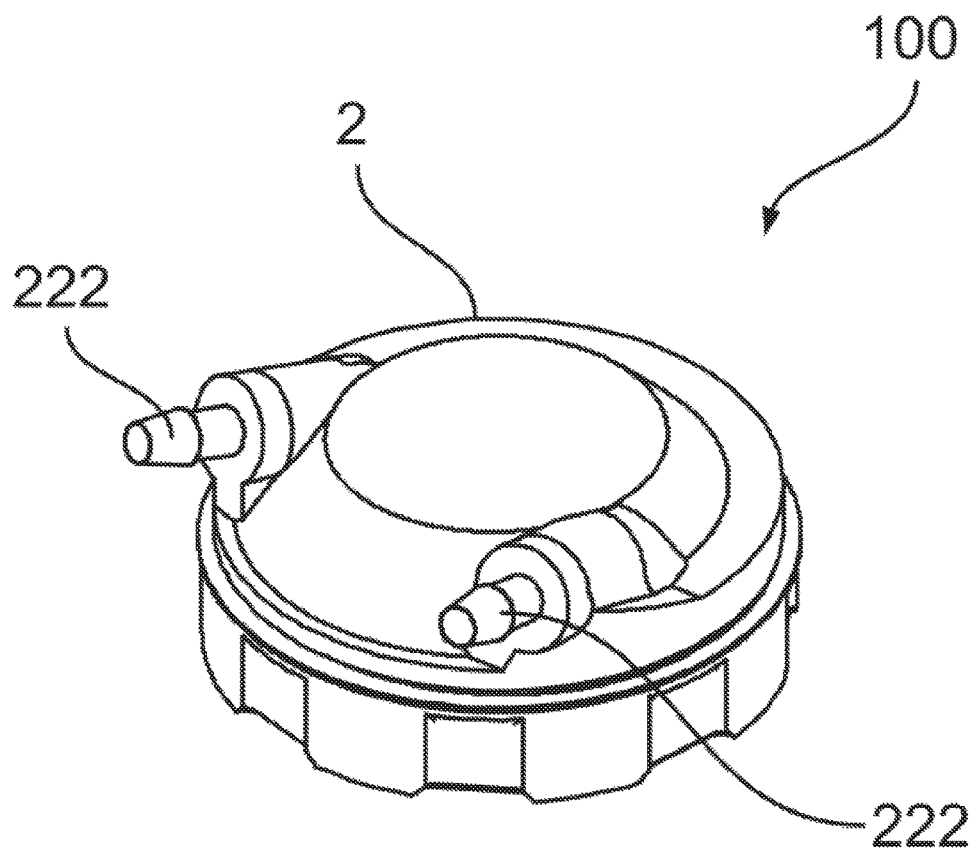
FIG. 7 is a schematic of an embodiment of the present invention having barbed port connectors.
Figure 8:
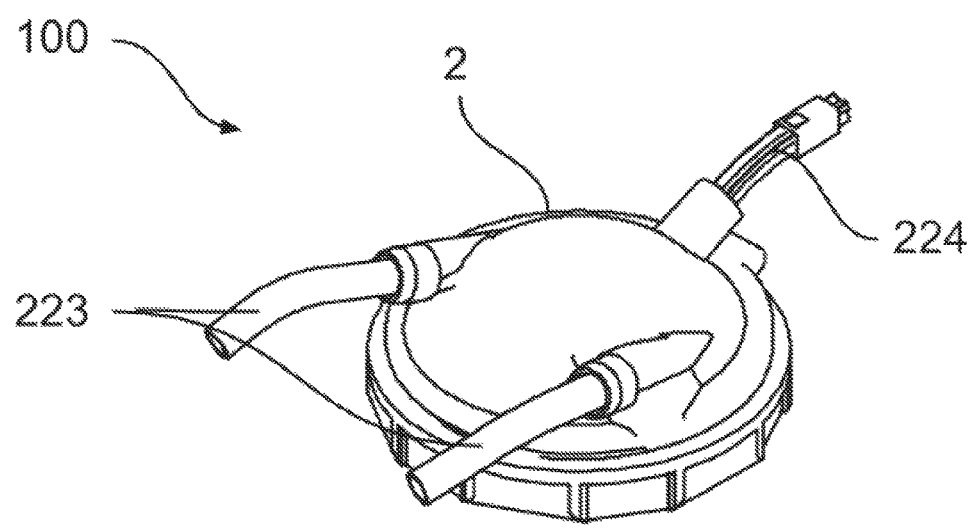
FIG. 8 is a schematic of an embodiment of the present invention having three access ports.

FIGS. 6-8 illustrate embodiments of Petri dish bioreactor 100 including an adapter body 2 with Luer angled ports 221, barbed angled ports 222, and angled ports 22 connected to fluid handling system connector 223 and monitoring sensor connector 224. The Luer angled ports 221 can be male or female. In some embodiments, as shown in FIG. 8, one of the angled ports 22 can act as an inlet and another angled port 22 as an outlet to facilitate flow through the Petri dish bioreactor 100. A fluid handling system including any number of reservoirs, pumps, fittings, and/or tubings can be connected to the angled ports 22 to provide automated perfusion. The fluid handling system connector 223 can be attached to angled ports 22 via the Luer angled ports 221 and the barbed angled ports 222. In some embodiments, the angled ports 22 may be hinged to allow a user to adjust the angle of the angled ports 22, between discrete angles or within a working range.

Figure 9:
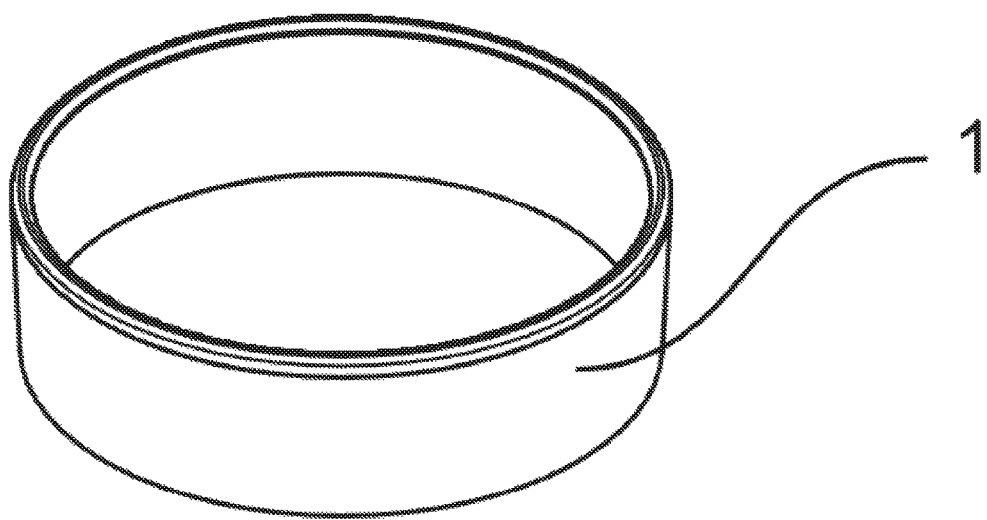
FIG. 9 is a schematic of a Petri dish.

FIG. 9 illustrates an embodiment of the Petri dish 1 as a culture plate with a cylindrical shaped sidewall and open top portion. Other geometric culture plates are also within the scope of the invention, including other arcuate, square, rectangular, polygonal, or other shapes. In some embodiments, the adapter compression cap 4 can incorporate the Petri dish 1 with diameter ranging between about 20 mm and about 150 mm. The Petri dish 1 can have a transparent bottom surface to allow passage of light from an imaging element (e.g., microscope condenser) through the Petri dish bioreactor 100 to a microscope objective. The bottom surface of the Petri dish 1 can be coated in a way that the bottom surface will allow light with certain range of frequency.

Figure 10:
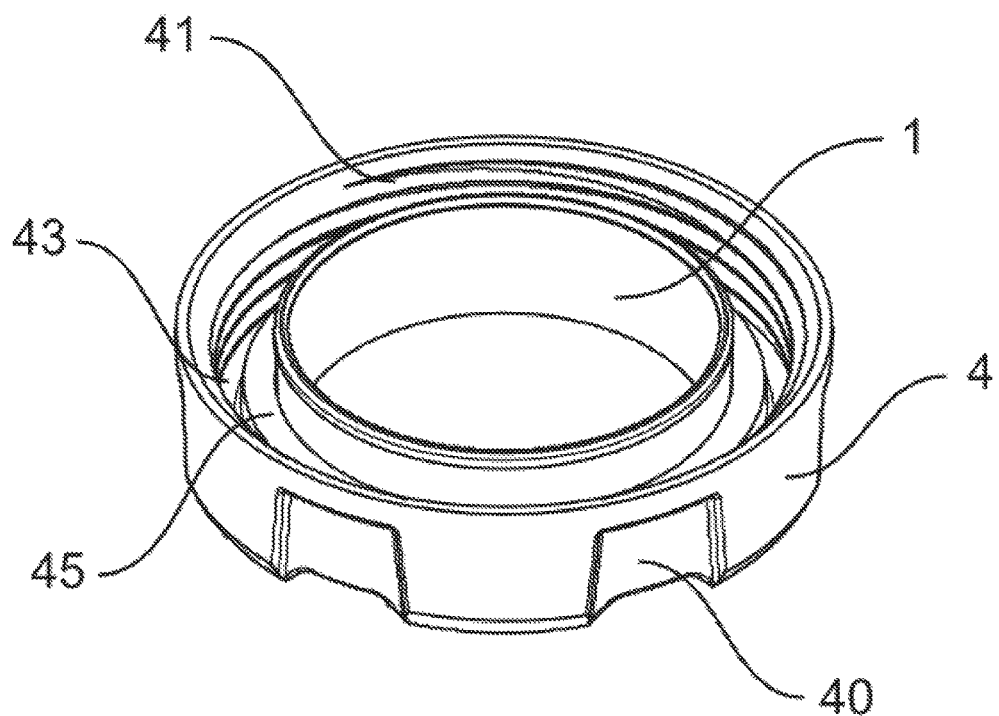
FIG. 10 is a schematic of a Petri dish mounted into an adapter compression cap.
Figure 11:
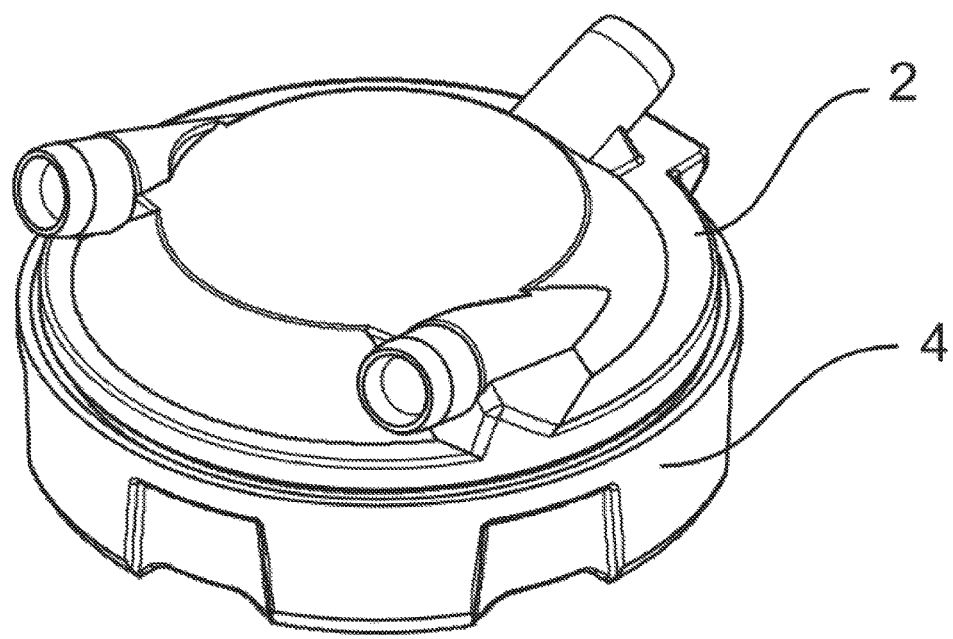
FIG. 11 is a schematic of a Petri dish bioreactor.

FIG. 10 is a schematic of the Petri dish 1 mounted within an adapter compression cap 4. In some embodiments, the adapter compression cap 4 can include a Petri dish ridge 45, a compression cap thread 41, grip indentations 40, and/or a containment moat 43. The functionality and description of the compression cap thread 41, the Petri dish ridge 45, and the grip indentations 40 can be as previously described. The containment moat 43 is defined as space between the compression cap thread 41 and the Petri dish ridge 45. The containment moat 43 can be configured to collect any leaked or overflow material from the Petri dish bioreactor 100. In some embodiments, a bottom surface of the containment moat 43 of the adapter compression cap 4 can be made out of an absorbent material such that if there is a leak from the Petri dish bioreactor 100, the bottom surface of the containment moat 43 can absorb the leak. FIG. 11 is an illustration of an adapter compression cap 4 as shown in FIG. 10, with an adapter body 2 illustrated as well.

Figure 12:
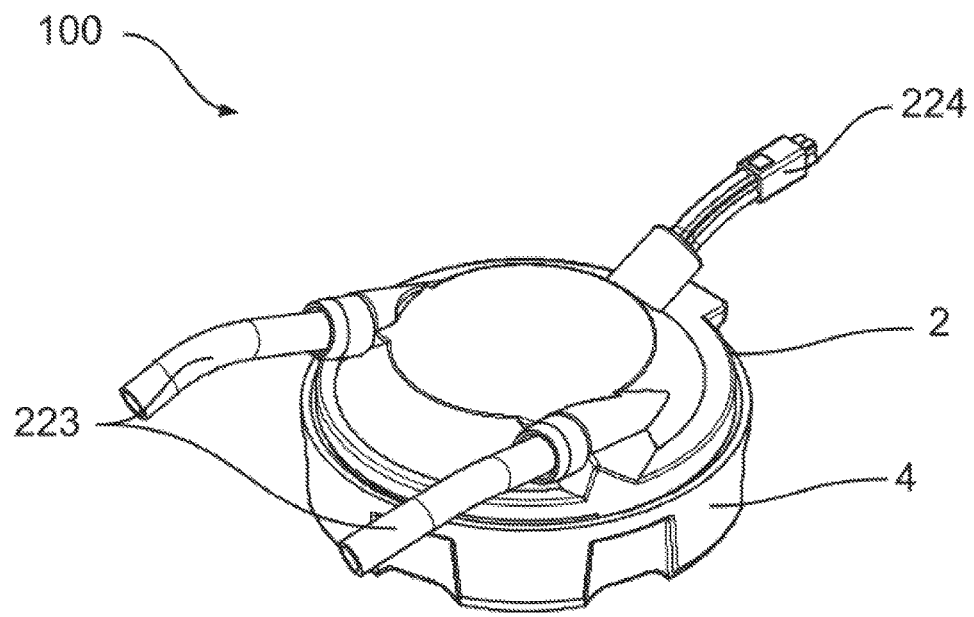
FIG. 12 is a schematic of a Petri dish bioreactor connected to a fluid handling system connectors and monitoring sensor connectors.

FIG. 12 is a schematic of a Petri dish bioreactor 100 with its angled ports 22 connected to a fluid handling system connector 223 and monitoring sensor connectors 224. In some embodiments, sensors may be adapted to the adapter body ports 22 to monitor chemistry and/or microenvironmental conditions of the bioreactor. These sensors can monitor conditions such as any number of pH, temperature, pressure, humidity, electrolytes, glucose, oxygen, and/or $CO_2$, among other parameters. Some embodiments include methods and devices to sense the internal bioreactor environment. Contactless sensing can be obtained by attaching sensors to the outside of the bioreactor. These contactless sensors can infer the bioreactor environment by measuring minor variations in signals such as voltage, current, resistance, capacitance, inductance, radiation, and temperature. Contact sensors can require the sensing portion of the probe be inside the bioreactor. Data can be transmitted wirelessly or through wires. Wired embodiments can require that the probe wire pass through a bioreactor Luer port.

In some embodiments, monitoring sensor connector 224 can be operatively connected to one of angled ports 22 of an adapter body 2, as shown in FIG. 8. Sensors operatively connected to the monitoring sensor connector 224 can monitor environmental conditions such as pH, temperature, oxygen concentration, dissolved oxygen, and flow rate in situations when the sensors are located upstream of the bioreactor to measure media conditions, when the sensors in the bioreactor measure extracellular conditions, and/or when the sensors located downstream of the bioreactor measure cellular waste conditions.

To keep the bioreactor watertight, a custom Luer cap can be utilized to seal the Luer port while allowing for wires to pass. The custom Luer port cap can be made of a soft, semi-soft, semi-rigid, or rigid material. Softer materials can conform to the sensor wires to provide a better watertight seal for the Luer port. One embodiment has the Luer port cap permanently fixed to the sensor wires. Another embodiment has the Luer port cap slotted and removable to allow for any wire configuration. The removable Luer cap embodiment allows for users to create custom sensors that fit into the Petri dish bioreactor. Any unused ports can be sealed off using an unslotted soft, semi-soft, semi-ridge, or ridge Luer port cap. Softer unslotted Luer port caps allow for higher internal pressures by creating a better seal between the plug and the Luer port. Harder unslotted Luer port caps provide a harder handle that may provide easier removal.

Figure 13:
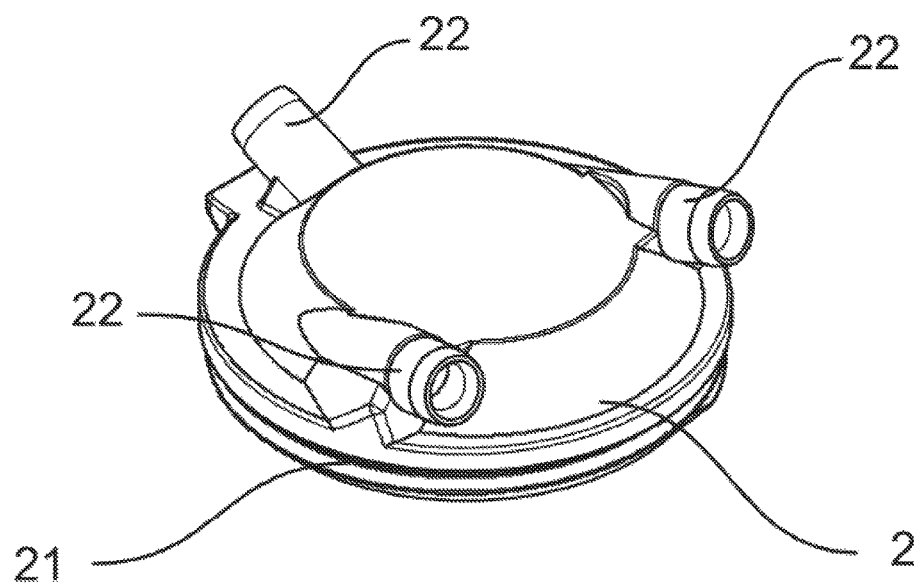
FIG. 13 is a schematic of an adapter body.

FIG. 13 is a schematic of an adapter body 2 including an adapter body thread 21 and angled ports 22 as previously described.

Figure 14:
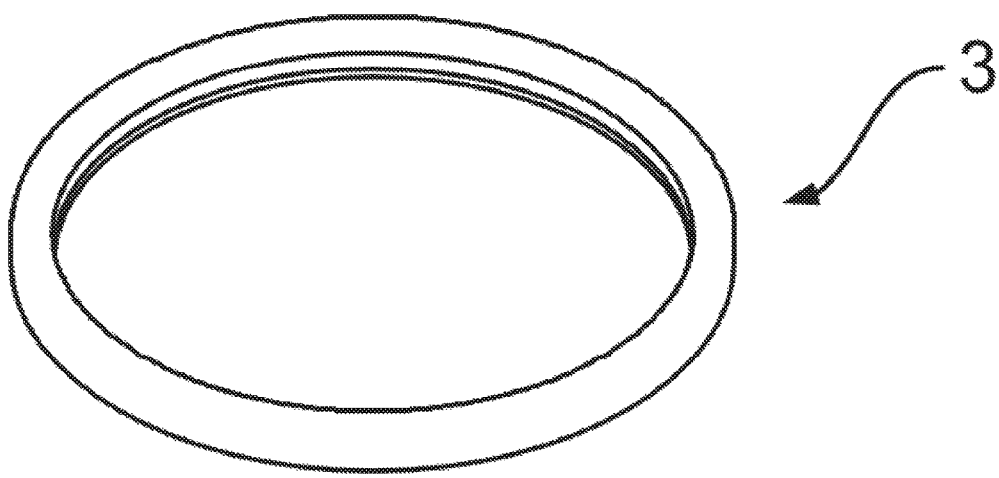
FIG. 14 is a schematic of an adapter body gasket.
Figure 15A:
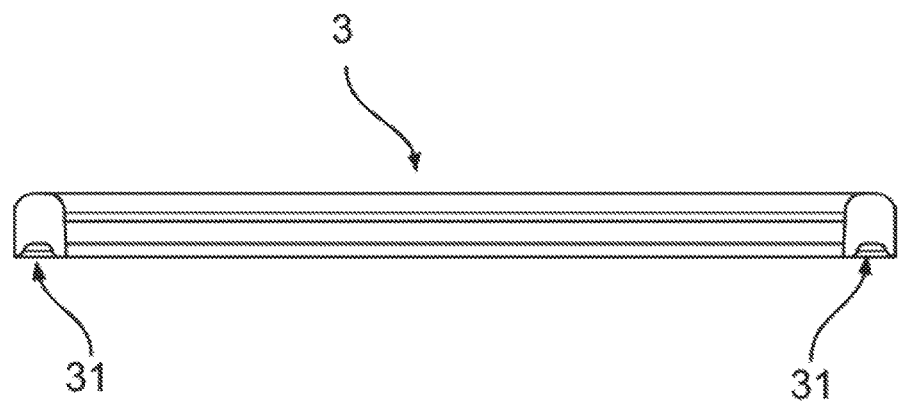
FIG. 15A is a cross-sectional view of an adapter body gasket showing a groove.
Figure 21:
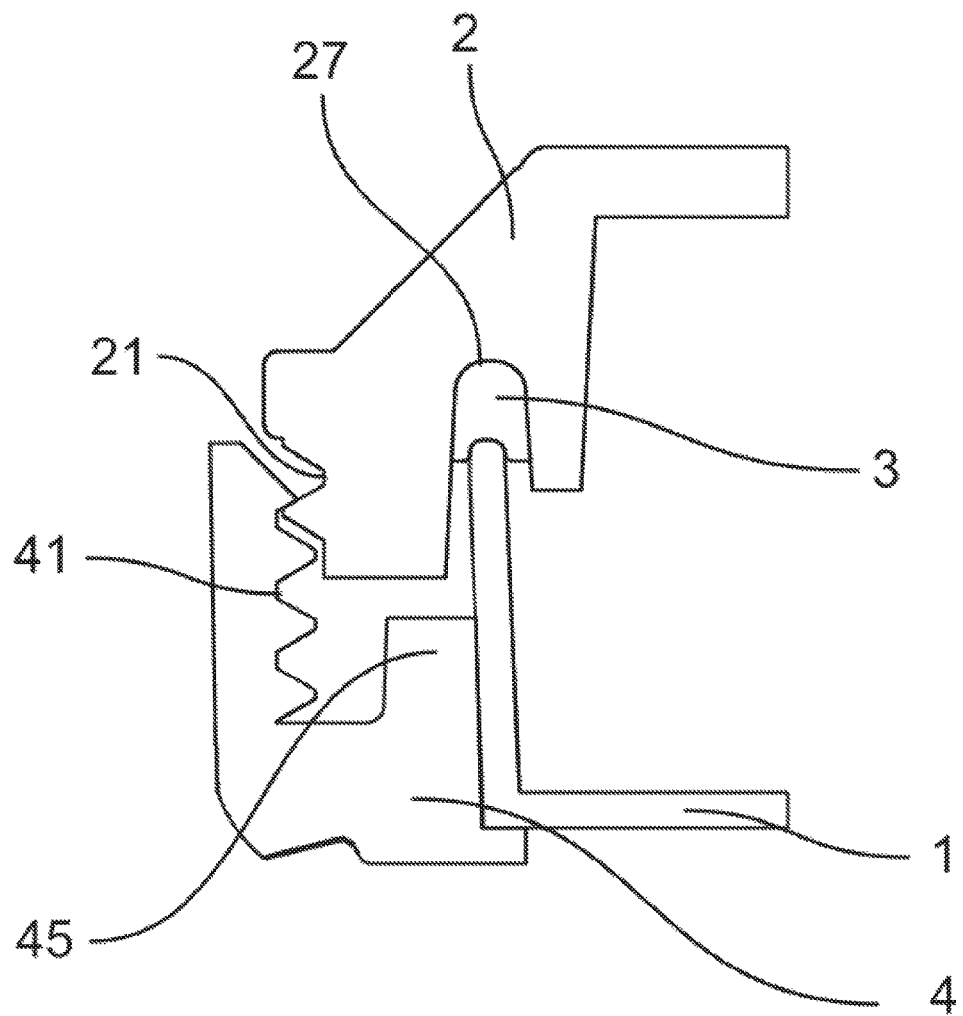
FIG. 21 shows a close-up view of a partial Petri dish bioreactor cross-section.
Figure 24:
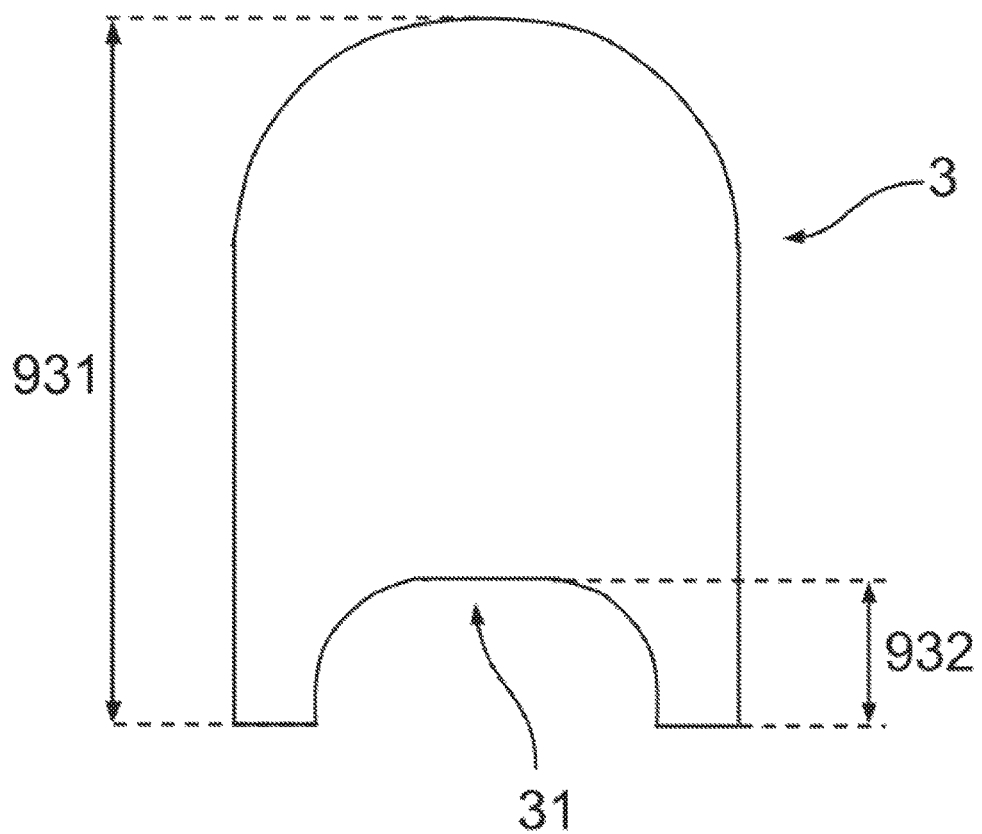
FIG. 24 shows a cross-section of a gasket with a groove.

FIGS. 14 and 15A show various views of a gasket 3. The gasket 3 can have a generally arcuate geometry as shown in some embodiments. In some embodiments, the gasket 3 has one, two, or more gasket grooves 31, which can be in some cases a concave surface defining an underside of the gasket 3. FIGS. 15A and 24 illustrate different cross-sectional views of the gasket 3 with a gasket groove 31. FIG. 21 particularly illustrates a gasket 3 interacting with an adapter body groove 27 of the adapter body 2 so that the gasket 3 is fixedly displaced within adapter body groove 27. The gasket groove 31 can define an underside of the gasket 3 which interacts with the sidewall of the Petri dish 1 so that the surface of the gasket groove 31 contacts with the top surface of the wall of the Petri dish 1. For example, the gasket groove 31 can engage the lip (e.g., the top edge of the lip) when the adapter compression cap 4 is compressed against the adapter body 2. When the adapter compression cap 4 is compressed against the adapter body 2, the lip of the sidewall of the Petri dish 1 is compressed against the gasket groove 31. When the Petri dish 1 is compressed against the gasket 3 and the gasket groove 31, the surface of the gasket groove 31 collapses against the wall of the Petri dish 1, creating a seal. The surface of the gasket groove 31 may include linear surfaces, curved surfaces, or any combination of linear and curved surfaces, and can be circumferentially continuous in some cases. The shape of the gasket groove 31 may allow precise and easy fitting and alignment of the Petri dish 1 when the adapter compression cap 4 is compressed against the adapter body 2. Gasket height 931 can in some embodiments vary between about 1 mm and about 5 mm, while in some embodiments gasket groove height 932 can vary between about 0.5 mm and about 4 mm. In some embodiments, the gasket groove height 932 can be about or no more than about 80%, 70%, 60%, 50%, 40%, 30%, 20%, 10%, 5%, or less than the height of the gasket 931, or ranges including any two of the aforementioned values. In some embodiments as shown in FIG. 24 for example, the gasket 3 can have a concave first end, a concave gasket groove 31 on a second end opposite the first end, and generally parallel and linear lateral walls. The concave gasket groove 31 can in some cases have a width that is less than the concave first end as shown, and have lateral straight segments that intersect at right angles to the lateral walls as shown.

Figure 25A:
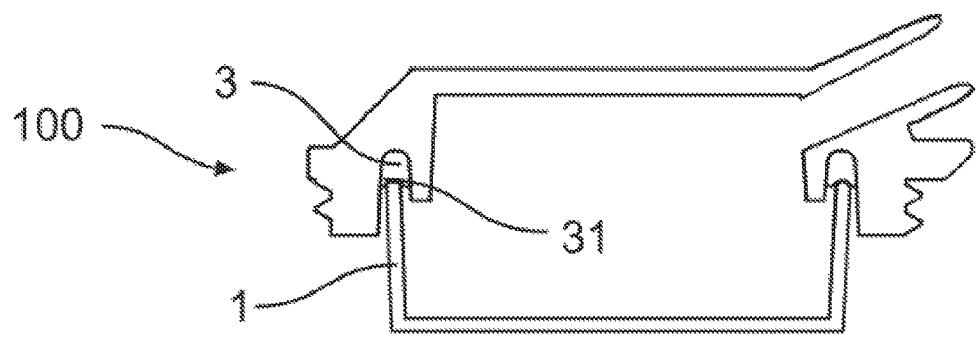
FIGS. 25A-25C show various types of gaskets in placed between an adapter compression cap and an adapter body without compression.
Figure 25B:
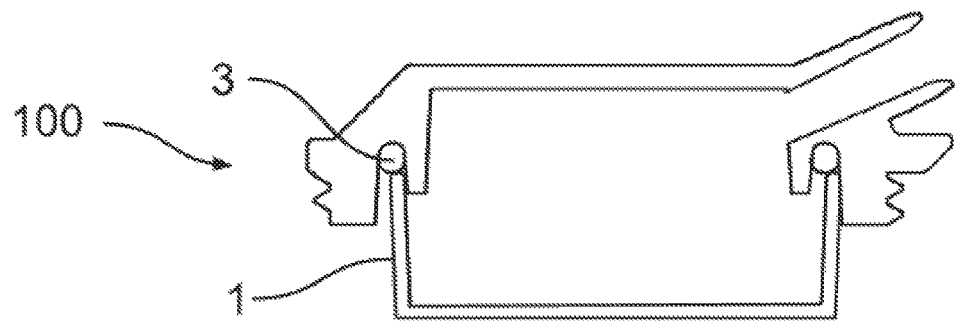
Figure 25C:
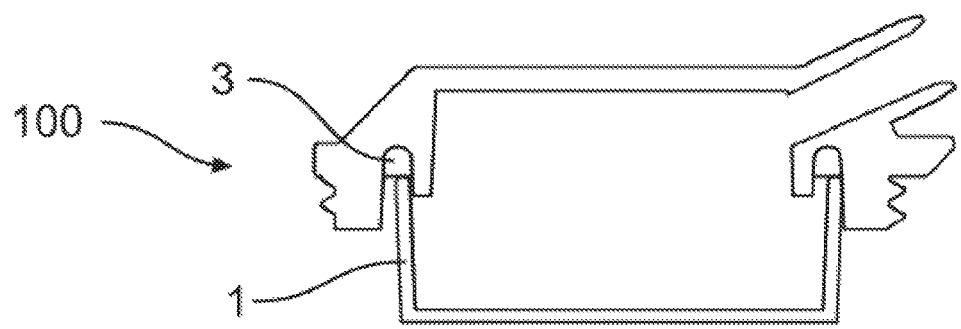
Figure 26A:
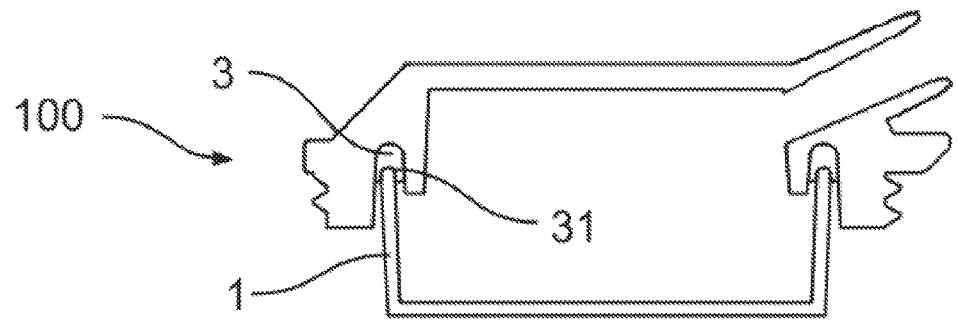
FIGS. 26A-26C show various types of gaskets in placed between an adapter compression cap and an adapter body with compression.
Figure 26B:
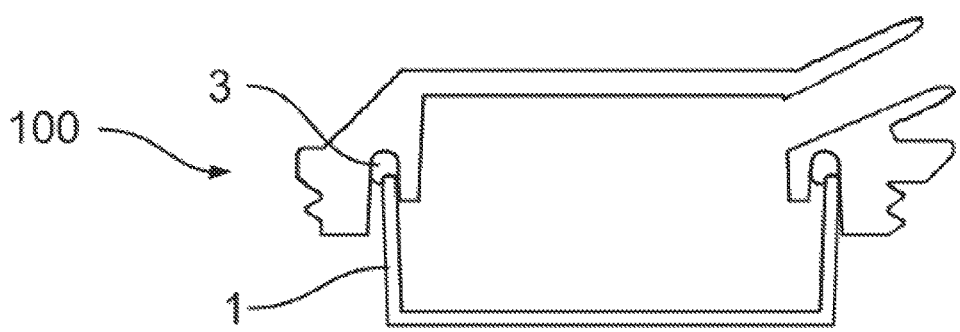
Figure 26C:
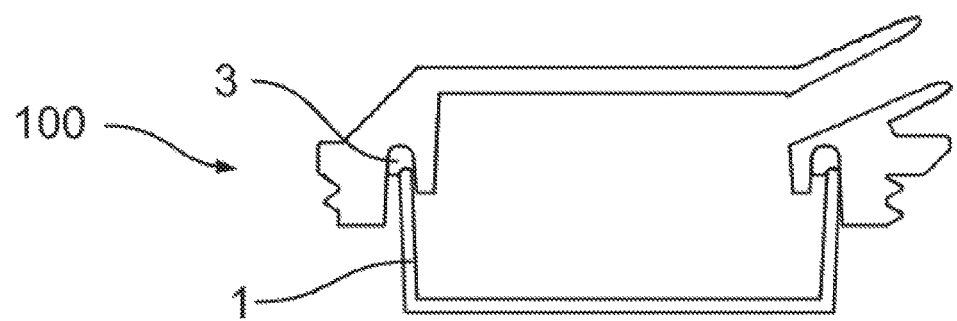
Figure 27:
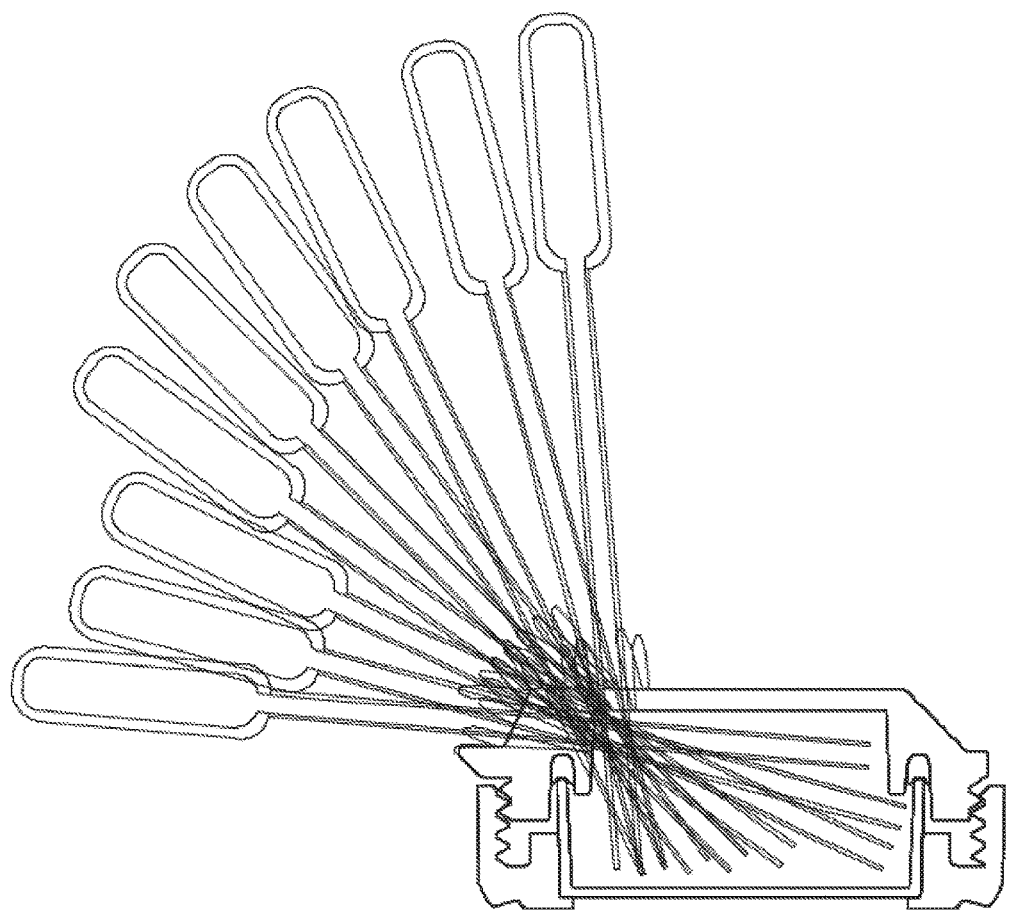
FIG. 27 is a diagram showing nine different non-limiting angular positions (5, 15, 25, 35, 45, 55, 65, 75, and 85 degrees) of angled ports incorporated to an adapter body and corresponding pipette positions.
Figure 28:
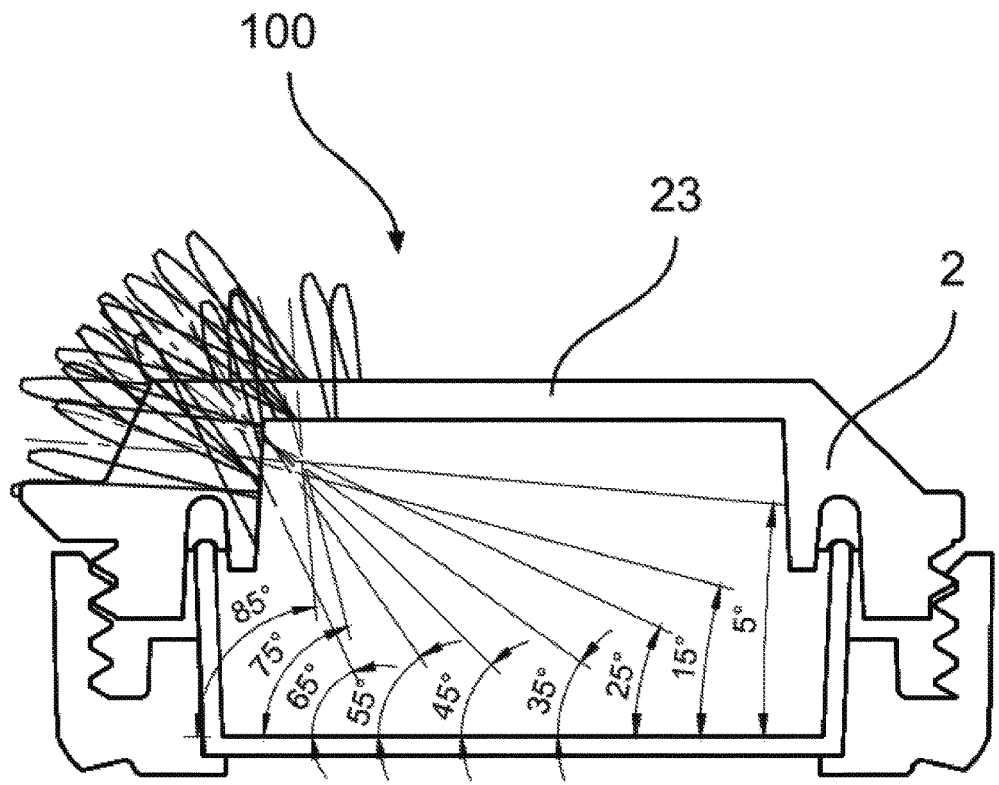
FIG. 28 is a diagram showing nine different non-limiting angular positions (5, 15, 25, 35, 45, 55, 65, 75, and 85 degrees) of angled ports with angular measurements.
Figure 29A:
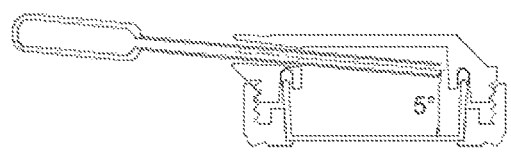
FIGS. 29A-29E show various angular positions of angled ports along with corresponding pipette positions with respect to the bioreactor.
Figure 29B:
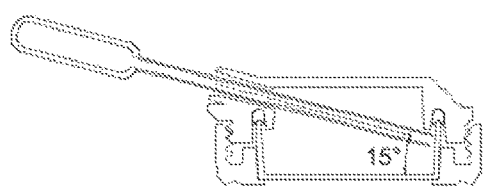
Figure 29C:
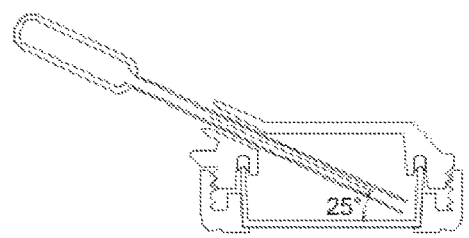
Figure 29D:
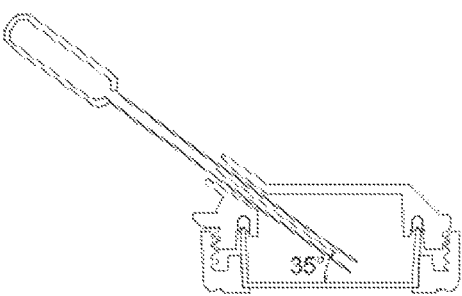
Figure 29E:
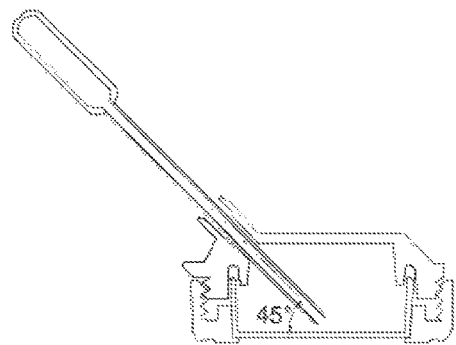
Figure 30A:
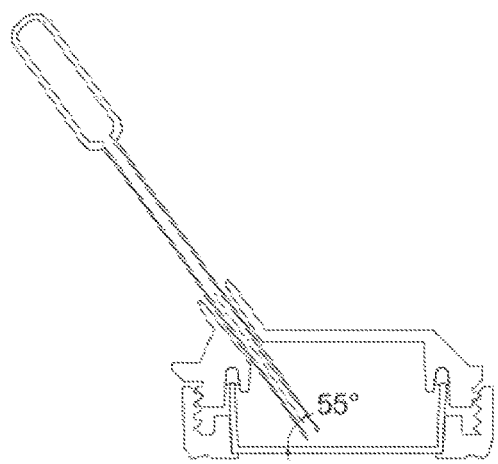
FIGS. 30A-30D shows various angular positions of angled ports along with corresponding pipette positions with respect to the bioreactor.
Figure 30B:
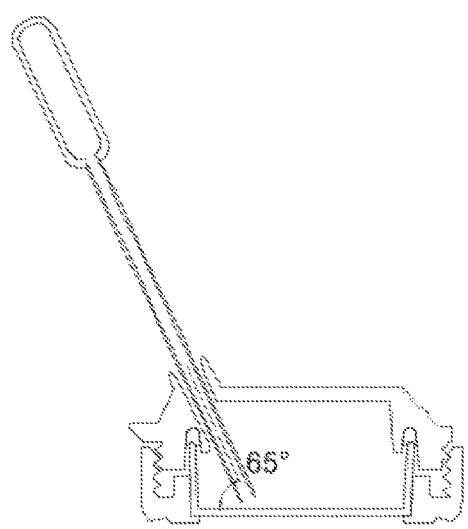
Figure 30C:
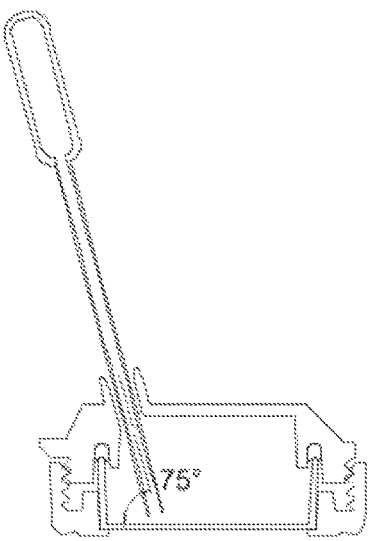
Figure 30D:
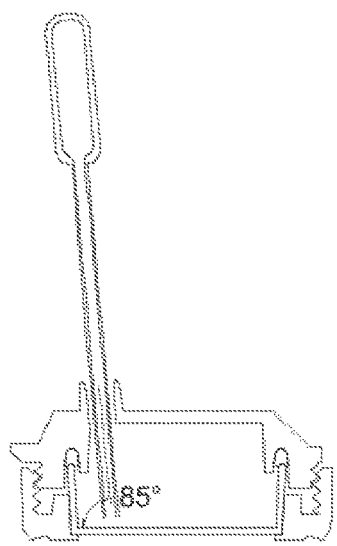

In some embodiment, the gasket groove 31 may be arcuate and concave to guide the Petri dish 1 to a concentric alignment to the gasket 3 and adapter body 2. As shown in FIGS. 25A and 26A, the concave-shaped gasket groove 31 increases the surface area of contract between the Petri dish 1 and the gasket 3, thus improving the seal for the Petri dish bioreactor 100. On the other hand, conventional gaskets with circular cross-sections and lacking grooves may not properly optimize the contact between the gasket 3 and the relatively thin walled Petri dish 1, as shown in FIGS. 25B, 25C, 26B, and 26C. Arcuate and convex surfaces of a traditional gasket with a circular cross-section can be used in some embodiments, but may not provide sufficient contact between the gasket 3 and the Petri dish 1 to create adequate watertight and/or airtight seals for the Petri dish bioreactor 100 in some cases. Moreover, gaskets with flat bottom surfaces can be used in some cases, although in other cases can potentially be prone to misalignment due to deformation along the vertical walls of the Petri dish 1.

In some embodiments, the gasket 3 may include a superior-facing surface and an inferior-facing surface, as well as lateral surfaces. The superior-facing surface and the inferior-facing surface may each include a gasket groove configured to mate with a sidewall of a culture plate. In some embodiments, the gasket groove may be a preformed concave groove configured to mate with a top portion of the sidewall of the culture plate. The surface of the gasket groove may also be substantially arcuate. The dimensions of an opening of the groove can be configured so that the width of the opening is substantially similar to the thickness of the sidewall of the culture plate. In some embodiments, the diameter of the opening of the groove is substantially similar to the thickness of the sidewall of the culture plate.

Figure 15B:
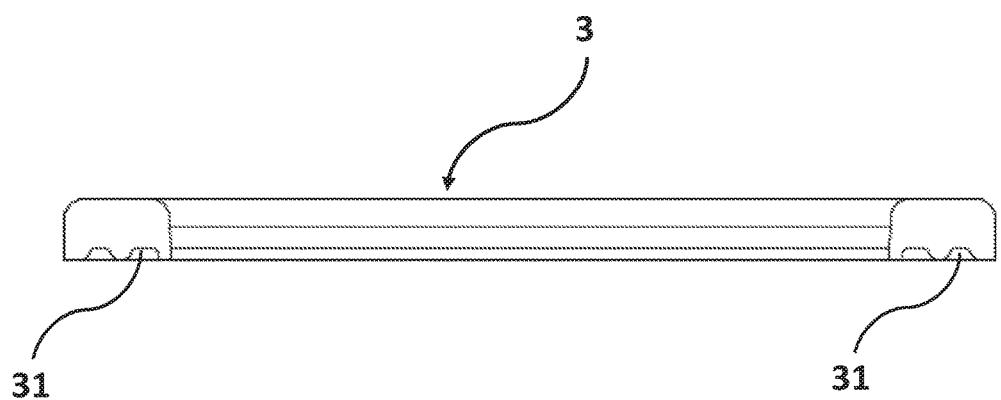
FIG. 15B is a cross-sectional view of an adapter body gasket showing more than one groove.
Figure 15C:
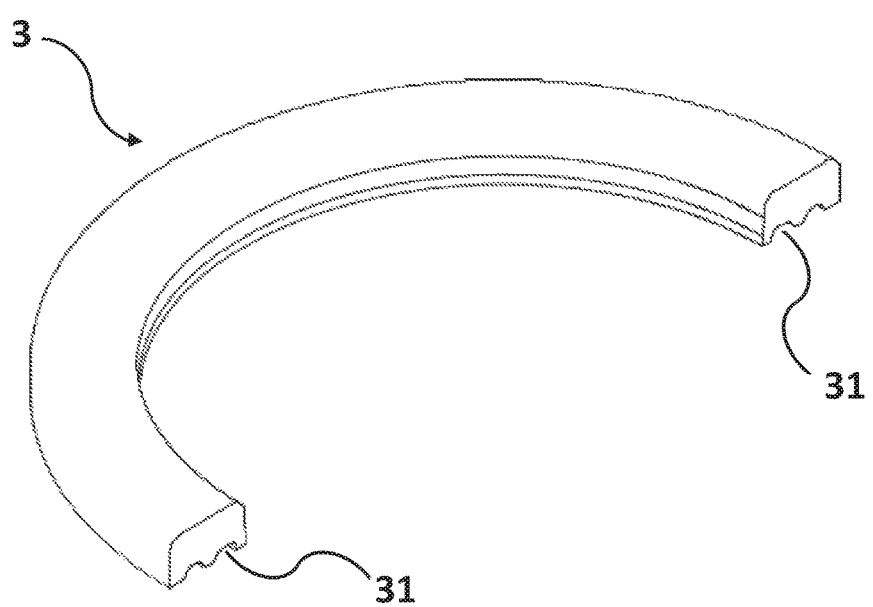
FIG. 15C is a perspective view of an adapter body gasket having more than one groove.

In some embodiments, as shown in FIGS. 15B and 15C, the gasket 3 may include more than one gasket groove 31, such as a plurality of gasket grooves 31 as shown, or about or at least about 2, 3, 4, or more gasket grooves in some cases. However, other embodiments can have no more than 1 (e.g., only a single) groove. The gasket grooves 31 may be dimensioned so that the opening of each of the gasket grooves receives the top portion of the sidewall of the culture plate. The width of each of the gasket grooves may be substantially equal to the width of the top portion of the sidewall of the culture plate. In some embodiments, the width of the openings may be greater than the width of the top portion of the sidewall of the culture plate. Having more than one gasket groove can advantageously allow an operator to use a "one size fits all" single gasket for culture plates with different diameters, in which one gasket groove can house a top portion of the sidewall of the culture plate while other gasket grooves can remain unused. Some of the gasket grooves may include arcuate surfaces and some may include linear surfaces. In some designs, all of the grooves have arcuate surfaces. In some other designs, all of the grooves have linear inner surfaces. The more than one gasket groove may be configured to have the same dimensions. In some other embodiments, the grooves may have different dimensions (e.g., widths) and/or shapes.

In some embodiments, the gasket 3 can include at least one adhesive surface to provide a better seal for a Petri dish bioreactor 100. The at least one adhesive surface can be a concave underside of the gasket 3 so that the concave underside can adhere to the top surface of the sidewall of a culture plate. A portion of the concave underside can be adhesive. However, the entire surface of the concave underside can be adhesive. The at least one adhesive surface can be one or more gasket grooves 31. The one or more gasket groove 31 can adhere to the top surface of the sidewall of a culture plate. In some embodiments, at least one of the portions of the gasket groove 31 that collapse against the sidewall of the culture plate can be adhesive. In some embodiments, the entire surface of the gasket groove 31 can be adhesive.

The at least one adhesive surface can be a top surface of the gasket 3 such that, when compressed against an adapter body gasket groove 27 of an adapter body 2, it can create a better seal between the gasket 3 and the adapter body gasket groove 27. In addition, adhesive top surface can prevent the gasket 3 from moving once placed within the adapter body gasket groove 27. In some embodiments, a portion of the top surface of gasket 3 can be adhesive. In some embodiments, the entire portion of the top surface of gasket 3 can be adhesive.

In some embodiments, the entire surface of the gasket 3 can be adhesive. In some embodiments, the entire surface of the gasket 3 can be non-adhesive (e.g., be devoid of any adhesive). In some embodiments, the gasket 3 can have both adhesive surfaces and non-adhesive surfaces. In some embodiments, the gasket 3 can contact the bottom surface of the culture plate. The gasket 3 can include at least one adhesive surface that can adhere to the bottom surface of the culture plate. The gasket 3 can also include one or more apertures. The gasket 3 can include an adhesive surface that adheres to the bottom surface of the culture plate. The gasket 3 can include one or more apertures. In some embodiments, the gasket 3 does not contact with the bottom surface of a culture plate inside the Petri dish bioreactor 100. The gasket 3 does not include apertures and it does not include adhesive surfaces in some cases.

Figure 16:
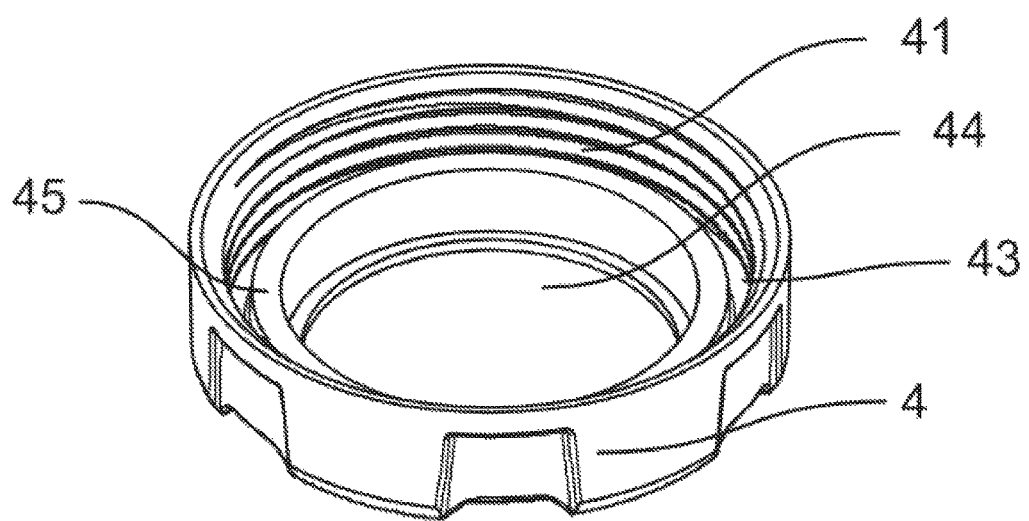
FIG. 16 is a schematic of an adapter compression cap.
Figure 17:
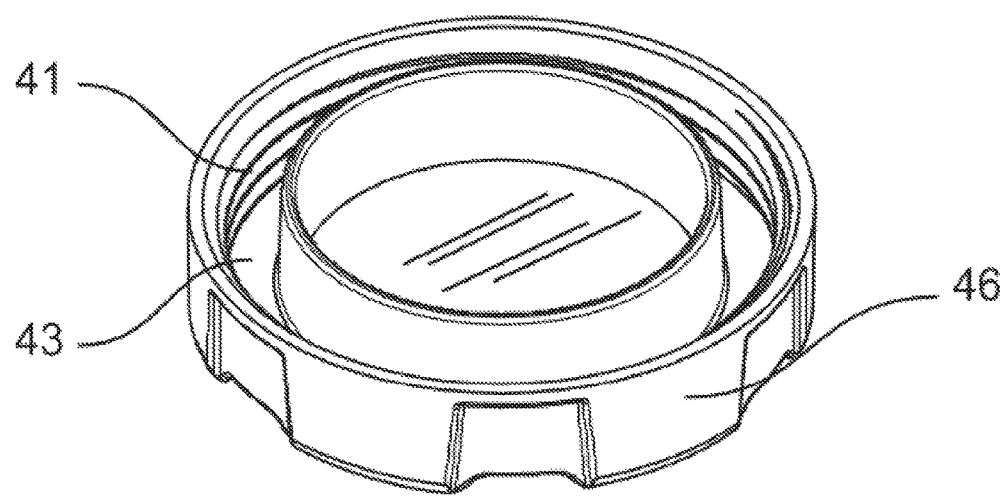
FIG. 17 is a schematic of a Petri dish integrated into the adapter compression cap.

FIG. 16 illustrates an embodiment of an adapter compression cap 4 including a compression cap thread 41, a containment moat 43, and a Petri dish ridge 45 as previously described. FIG. 17 illustrates an embodiment of an integrated compression cap 46. The integrated compression cap 46, as opposed to the adapter compression cap 4 as shown in FIG. 16, includes a built-in Petri dish. For example, the built-in Petri dish of the integrated compression cap 46 can be disposed in a substantially the same location as the Petri dish slot 44 of the adapter compression cap 4 as shown in FIG. 16. The integrated compression cap 46 can also include a compression cap thread 41 and a containment moat 43. The bottom surface of the integrated compression cap 46 can be a transparent surface to allow passage of light from an imaging element (e.g., microscope condenser) through the Petri dish bioreactor 100 to a microscope objective. The bottom surface can be treated or coated with other materials to only allow light with certain frequencies or wavelengths. The bottom surface of the integrated compression cap can be modified to have a glass bottom wherein a glass coverslip is attached externally or internally covering an opening created on the bottom of the compression cap. In some embodiments, the built-in Petri dish of the integrated compression cap 46 has threads incorporated to the top of arcuate wall of the built-in Petri dish. The threads can be incorporated on an outer surface of the arcuate wall or incorporated on an inner surface of the arcuate wall of the built-in Petri dish. The threads on the built-in Petri dish may be configured to operatively interact with the threads of an adapter body.

Figure 18:
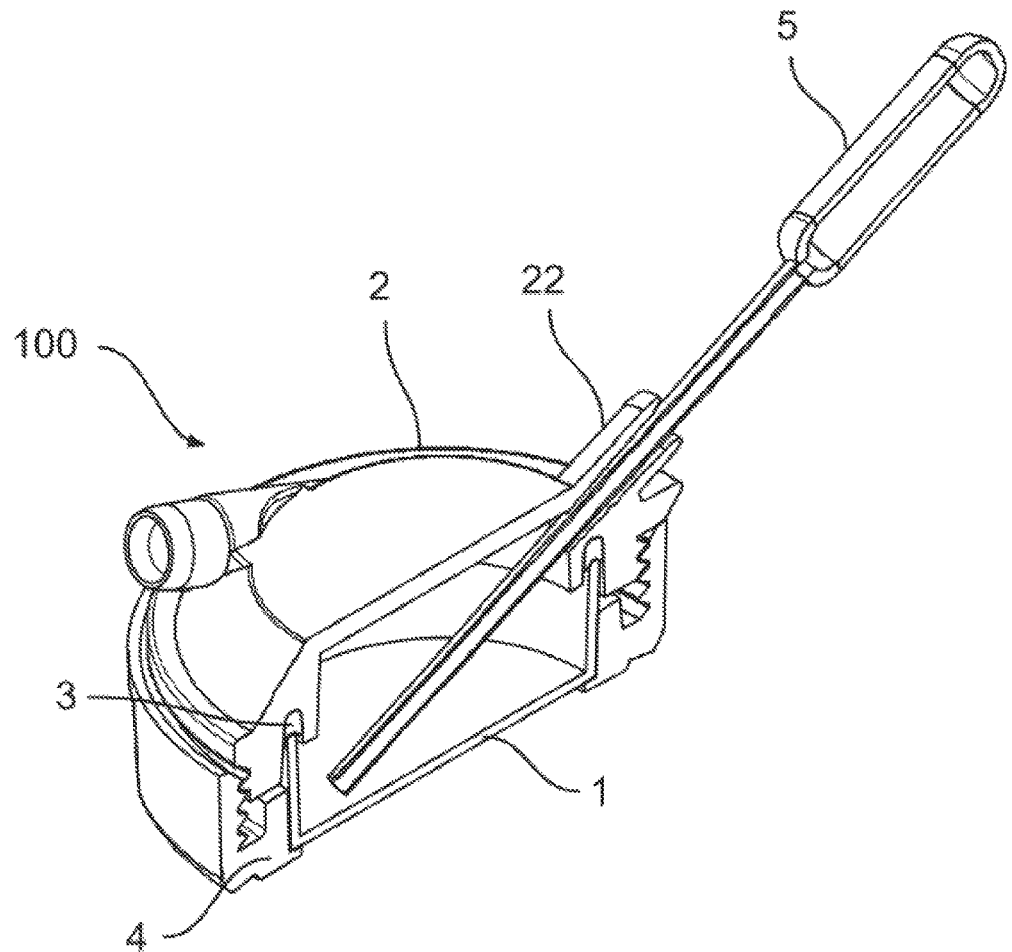
FIG. 18 is a cross-sectional view of a pipette inserted into an angle bioreactor port.
Figure 19:
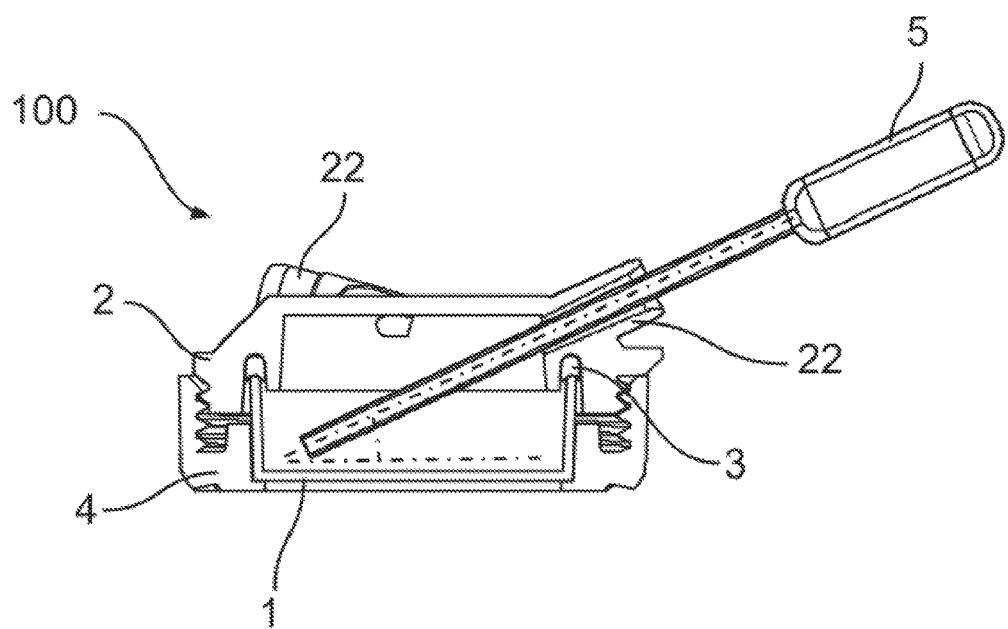
FIG. 19 is a cross-sectional view of a pipette inserted into an angle bioreactor port allowing for a low profile for microscopy applications that use short working distance condensers.
Figure 20:
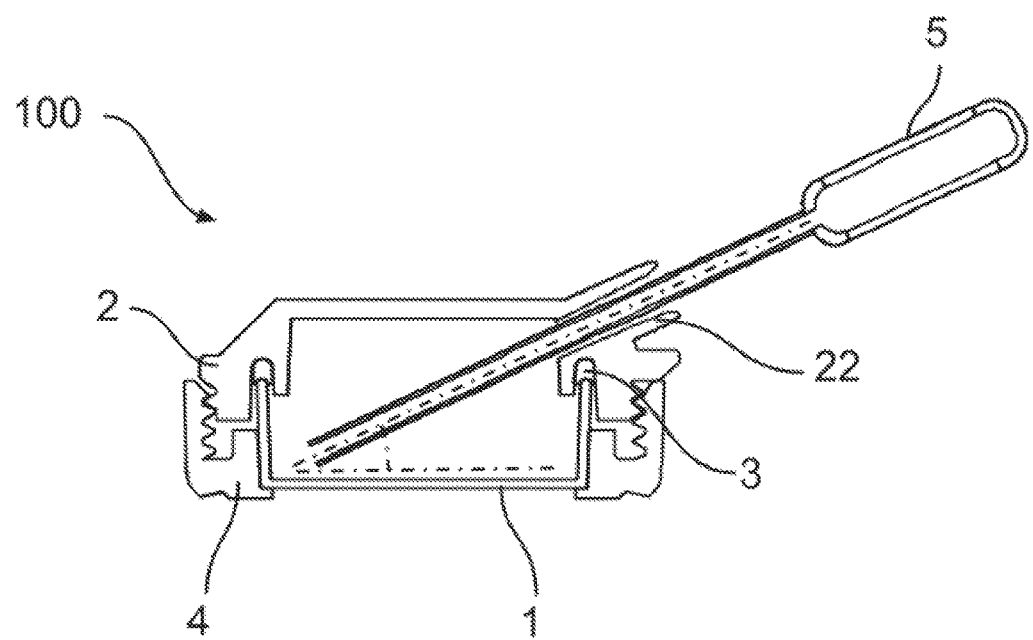
FIG. 20 is a section view of a pipette inserted into an angled bioreactor port.
Figure 22:
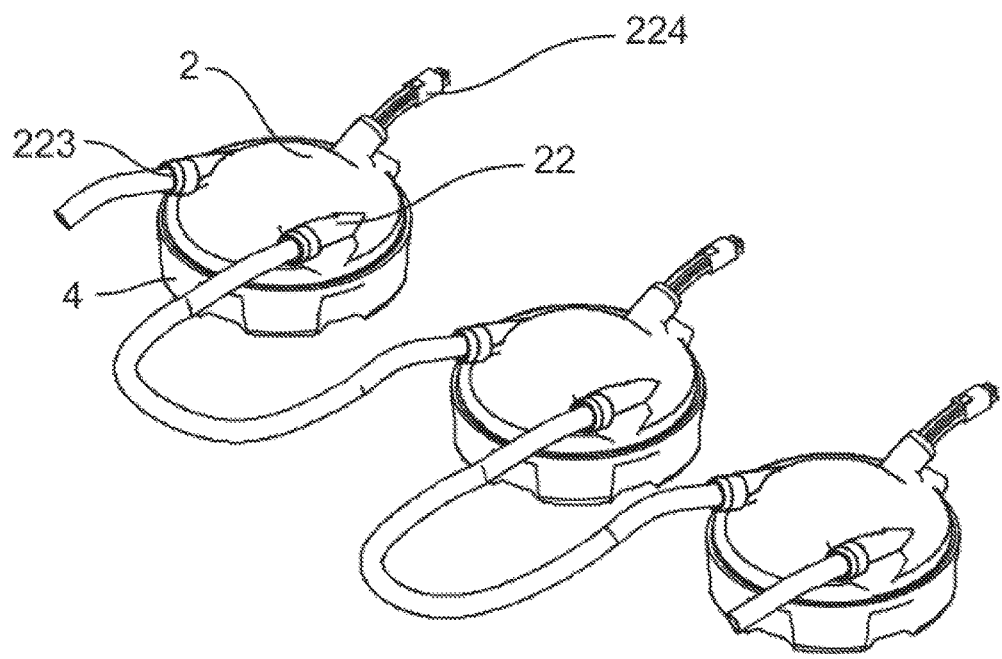
FIG. 22 shows an example embodiment of multiple Petri dish bioreactors connected in series.

FIGS. 18-20 show cross-sectional views of an embodiment of a Petri dish bioreactor 100. In this example embodiment, the Petri dish bioreactor 100 includes a Petri dish 1, an adapter compression cap 4, a gasket 3, and an adapter body 2 with at least one angled port 22. The angled port 22 provides access to the Petri dish bioreactor 100 so that a transfer pipette 5 can be inserted through the angled ports 22 into the Petri dish bioreactor 100 at a certain angle as shown in FIG. 22.

FIG. 21 illustrates a cross-sectional view of a Petri dish bioreactor 100 including a Petri dish 1, an adapter body 2, a gasket 3, and an adapter compression cap 4. The adapter compression cap 4 may incorporate an adapter compression cap thread 41, a containment moat 43, a Petri dish slot 44, and a Petri dish ridge 45. The ridge 45 may protrude upwards from the bottom portion of the adapter compression cap 4 and may be used to prevent the Petri dish 1 from moving. The ridge 45 defines the Petri dish slot 44. Some embodiments may incorporate the Petri dish slot 44 for the Petri dish 1 to prevent the Petri dish 1 from moving. The Petri dish ridge 45 may be fully annular around the vertical axis aligned at the center of the adapter compression cap 4. In some embodiments, the Petri dish ridge 45 may not be fully annular around the vertical axis aligned at the center of the adapter compression cap 4. The adapter body 2 may include an adapter body gasket groove 27 and an adapter body thread 21. The adapter body gasket groove 27 defines a slot where the gasket 3 may be placed. The adapter body thread 21 corresponds to the compression cap thread 41. In some embodiments, the adapter body thread 21 is a female threading and the adapter compression cap thread 41 is a corresponding male thread. In other embodiments, the adapter body thread 21 may be a male thread and the compression cap thread 41 may be a corresponding female thread.

Some embodiments may incorporate various types of snap-fit mechanisms. For example, an adapter body 2 may incorporate a full-parameter annular snap mechanism and an adapter compression cap 4 may incorporate a corresponding groove for the annular snap of the adapter body 2. When the adapter compression cap 4 is pushed against the adapter body 2, the annular snap of the adapter body 2 latches into the corresponding groove of the adapter compression cap 4, thus creating compression between the adapter body 2 and the adapter compression cap 4. The snap component may be incorporated to the adapter compression cap 4 and the corresponding groove may be incorporated in the adapter body 2. Some other embodiments may instead incorporate a partial-parameter annular snap mechanism or use multiple snaps at various locations.

In an aspect of the invention, the shape of an adapter body 2 and an adapter compression cap 4 are optimized to minimize area of debris entrapment. In some embodiments, the adapter body 2 and the adapter compression cap 4 are designed have dimensions to fit within a microscope stage supporting Petri dish diameters in the range from about 20 mm to about 150 mm, such as about 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm, 140 mm, 145 mm, 150 mm, or ranges including any two of the aforementioned values. The general shape and dimension of the adapter body 2 and the adapter compression cap 4 may vary depending on the corresponding Petri dish 1. The general shape and dimension of the adapter body 2 and the adapter compression cap 4 may vary depending on the microscope utilized. For example, height of a Petri dish bioreactor 100 can be limited by the spatial constraints of a viewing instrument utilized.

In some embodiments, it can be advantageous that an adapter body 2 and an adapter compression cap 4 are aligned such that their respective horizontal axis are parallel to each other. Misalignment between the adapter body 2 and the adapter compression cap 4 can result in the misalignment between a light transmission window 23 of the adapter body 2 and a clear bottom surface of the adapter compression cap 4. If those two surfaces are not parallel, there may be artifacts with some microscopy techniques.

Figure 23:
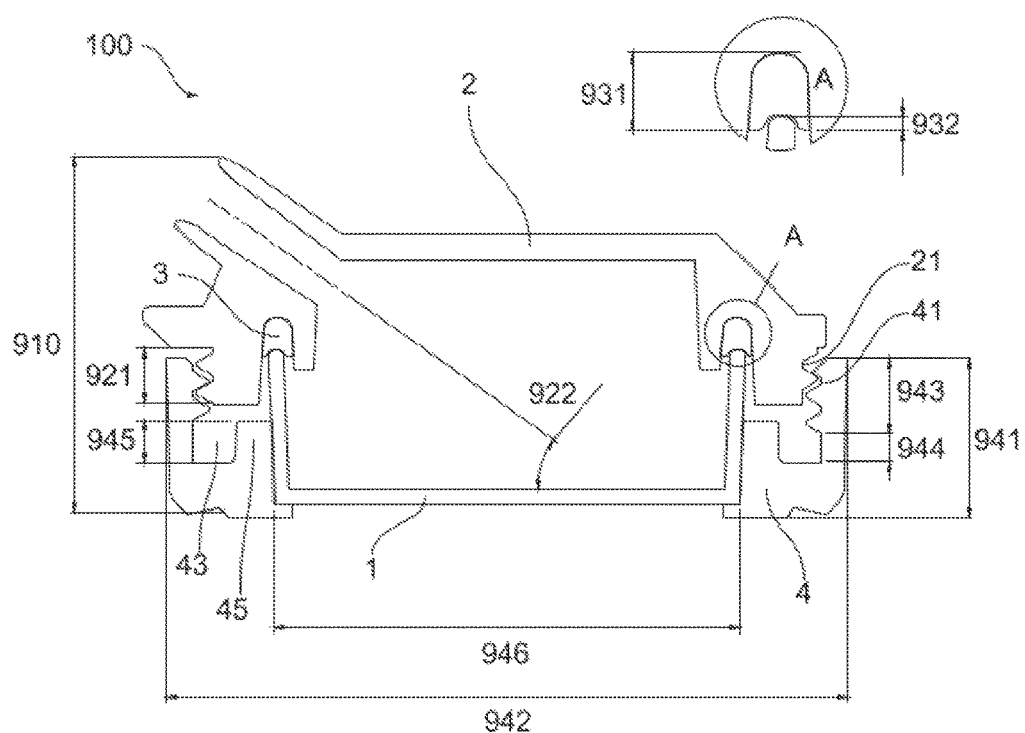
FIG. 23 shows non-limiting examples of dimensions for various elements of a bioreactor system.

FIG. 23 illustrates non-limiting potential dimensions for various features of the Petri dish bioreactor 100. In some embodiments, the Petri dish bioreactor 100 can have a height 910, which in some cases is between about 5 mm and about 50 mm, about 10 mm and about 50 mm, between about 15 mm and about 35 mm, or about 5 mm, 10 mm, 15 mm, 20 mm, 25 mm, 30 mm, 35 mm, 40 mm, 45 mm, 50 mm, or ranges including any two of the aforementioned values. In some embodiments, the Petri dish bioreactor height 910 is larger than the height of a standard Petri dish, but smaller than the working distance of an external device, such as an external diagnostic or therapeutic devices such as an inverted microscope condenser.

In some embodiments, an adapter body 2 has an adapter body thread 21 with a length 921, which in some cases is between about 0.5 mm and about 15 mm, about 1 mm and about 10 mm, between about 3 mm and about 5 mm, or about 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, or ranges including any two of the aforementioned values. The adapter body thread 21 should be long enough to create a watertight and airtight seal, but not long enough to inconvenience the user. In some embodiments, the adapter body 2 has at least one angled ports 22 at an angle 922, which in some cases is between about 5 degrees and about 75 degrees, between about 5 degrees and about 15 degrees, between about 25 degrees and about 55 degrees, or about 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or ranges including any two of the aforementioned values. It is important to note that as the Petri dish diameter increases, a smaller angle is more appropriate in some cases.

In some embodiments, a gasket 3 has a height 931, which in some cases is between about 0.5 mm and about 10 mm, between about 1 mm and about 5 mm, between about 1 mm and about 3 mm, or about 0.5 mm, 1 mm, 2 mm, 3 mm, 4 mm, 5 mm, 6 mm, 7 mm, 8 mm, 9 mm, 10 mm, or ranges including any two of the aforementioned values. The gasket height 931 should be, in some cases, large enough to hold the gasket 3 into the adapter body 2 using wall friction. The gasket height 931 should also be, in some cases, large enough to allow for suitable compression to create a watertight and airtight seal. In some embodiments, the gasket 3 has a gasket groove 31 that has a height 932, which in some cases is between about 0.5 mm and about 5 mm, between about 1 mm and about 4 mm, between about 2 mm and about 3 mm, or about 0.5 mm, 1 mm, 1.5 mm, 2 mm, 2.5 mm, 3 mm, 3.5 mm, 4 mm, 4.5 mm, 5 mm, or ranges including any two of the aforementioned values. The gasket groove height 932 should be large enough to seat a Petri dish 1 in some cases.

In some embodiments, an adapter compression cap 4 has a height 941, which in some cases is between about 3 mm and about 30 mm, between about 5 mm and about 25 mm, between about 10 mm and about 20 mm, or about 3 mm, 5 mm, 10 mm, 15 mm, 20 mm, 25 mm, 30 mm, or ranges including any two of the aforementioned values. The compression cap height 941 should be large enough in some cases to provide a good grip for the user while being short enough to allow the Petri dish bioreactor 100 to fit in an inverted microscope. The compression cap height 941 should also be large enough in some cases to allow for enough internal threading to create watertight and airtight seal. In some embodiments, the adapter compression cap 4 has a diameter 942, which in some cases is between about 15 mm and about 200 mm, between about 25 mm and about 170 mm, between about 50 mm and about 150 mm, or about 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm, 140 mm, 145 mm, 150 mm, 155 mm, 160 mm, 165 mm, 170 mm, 175 mm, 180 mm, 185 mm, 190 mm, 195 mm, 200 mm, or ranges including any two of the aforementioned values. The compression cap diameter should be sized to friction fit 20 to 170 mm Petri dishes. In some embodiments, the adapter compression cap 4 has compression cap thread 41 with length 943, which in some cases is between about 1 mm and about 15 mm, between about 5 mm and about 10 mm, between about 1 mm and about 10 mm, or about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, or ranges including any two of the aforementioned values. The compression cap thread length 943 should be long enough to create a watertight and airtight seal, but not long enough to inconvenience the user.

In some embodiments, the adapter compression cap 4 has a containment moat 43 with a height containment moat height 945, which in some cases is between about 1 mm and about 20 mm, between about 5 mm and about 15 mm, between about 5 mm and about 10 mm, or about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or ranges including any two of the aforementioned values. The containment moat height 945 should be tall enough to hold the fluid overflow while not interfere with the closing of the Petri dish bioreactor 100. In some embodiments, the adapter compression cap 4 has a Petri dish slot 44 with a diameter 946, which in some cases is between about 15 mm and about 200 mm, between about 25 mm and about 170 mm, between about 50 mm and about 150 mm, or about 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, 100 mm, 105 mm, 110 mm, 115 mm, 120 mm, 125 mm, 130 mm, 135 mm, 140 mm, 145 mm, 150 mm, 155 mm, 160 mm, 165 mm, 170 mm, 175 mm, 180 mm, 185 mm, 190 mm, 195 mm, 200 mm, or ranges including any two of the aforementioned values. The compression cap friction-fit Petri dish slot diameter should be sized to fit about 15 mm to about 200 mm Petri dishes.

In some embodiments, the adapter compression cap 4 has a portion of its outer arcuate wall that defines an outer edge of the containment moat 43, wherein the portion of the arcuate wall is unthreaded, and wherein the unthreaded portion has a length 944, which in some cases is between about 0 mm and about 20 mm, between about 5 mm and about 15 mm, between about 5 mm and about 10 mm, or about 0 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or ranges including any two of the aforementioned values. The thread, however, can reach the bottom of the containment moat 43. Alternatively, the compression cap thread 41 can stop before reaching the bottom of the containment moat 43, creating a smooth walled moat.

In some embodiments, the Petri dish bioreactor 100 has a Petri dish 1 with a diameter, which in some cases is between about 20 mm and about 100 mm, between about 10 mm and about 150 mm, between about 20 mm and about 150 mm, or about 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, or ranges including any two of the aforementioned values.

The adapter compression cap 4 can be sufficient in size to house aforementioned Petri dish 1 and compression cap diameter 942 may range between 25 mm and 170 mm. For example, the Petri dish 1 may be 50 mm in diameter and the adapter compression cap 4 may have a diameter of 80 mm to accommodate for a Petri dish slot 44 for the Petri dish 1, a Petri dish ridge 45 defining the Petri dish slot 44, a containment moat 43, and compression cap thread 41. In addition, compression cap Petri dish slot diameter 946 can approximate the diameter of the Petri dish 1. Compression cap height 941 can be sufficient to provide a good grip for a user while being short enough to allow the Petri dish bioreactor 100 to fit between a condenser and a stage of a viewing instrument (e.g., microscope). The compression cap height 941 may vary between, for example, about 5 mm and about 25 mm. Adapter body thread length 921 and compression cap thread length 943 may be long enough to create a watertight and airtight seal. In some embodiments, adapter body thread length 921 and compression cap thread length 943 may be different. In some embodiments, the compression cap thread length 943 may be at a length to allow the compression cap thread 41 to accommodate adapter body thread 21 with different adapter body thread length 921. The compression cap thread length 943 may vary between 1 mm and 10 mm and the adapter body thread length 921 may also vary between 1 mm and 10 mm. They, however, may not exceed the compression cap height 941. In some embodiments, a containment moat 43 has containment moat height 945 that is sufficient to hold fluid overflow while not interfering with closing of the Petri dish bioreactor 100. The containment moat height 945 may vary between 1 mm and 15 mm but may not exceed the compression cap height 941.

In some embodiments, an adapter body 2 can include at least one or more angled ports 22 as previously described and illustrated. The angled ports 22 may be sealed with water-tight and air-tight port caps or accept connectors for tubing, or include one-way valves for example. The angled ports 22 may be molded with, overmolded with, or bonded to the adapter body. In some embodiments, the angled ports 22 have shapes that allow for custom attachments to fluid handling systems including pumps and/or vacuum depending on the desired clinical results. In some embodiments, as shown in FIG. 6, the angled ports 22 have standard connectors such as, for example, Luer, or Luer locking connectors. The horizontal position of the ports 22 as they connect to an internal aspect of the adapter body 2 can vary and will determine the volume of air gap within the Petri dish bioreactor 100. The adapter body ports may also incorporate standard connectors such as barbed connectors as shown in FIG. 7.

The angled ports 22 may be angled sufficiently to permit an access for a transfer pipette 5 to the bottom of the Petri dish 1 while not obscuring the central microscopic viewing area. The adapter body ports 22 may be angled at an acute angle, as shown in FIG. 20, with respect to an axis horizontal to the bottom surface of the Petri dish 1 or the bottom surface of the adapter compression cap 4. The angled configuration in some cases advantageously allows for a thinner profile for short working distance microscope condensers, and prevents spillage through the adapter body ports 22.

The angle and location of the angled ports 22 can impact microscopic viewing of the environment within the Petri dish bioreactor 100. FIGS. 27-30D are schematic diagrams depicting the adapter body ports 22 at various angles. In some embodiments, the adapter body ports 22 are angled between about 15 degrees and about 65 degrees, or at about, at least about, or no more than about 15, 20, 25, 30, 35, 40, 45, 50, 55, 60, or 65 degrees, or at ranges including any two of the aforementioned angles. Each of the adapter body ports 22 may be angled at the same or substantially the same angle from one another, or different angles in some embodiments. In some embodiments, the angles disclosed herein can be utilized for approximately 100 mm diameter culture plates, and/or other diameter plates as disclosed elsewhere herein.

While they can be utilized in some embodiments, angled ports 22 oriented at or approximately at a zero degree angle with respect to the horizontal axis of the bottom surface of the Petri dish 1 may disadvantageously allow leaks without a plug. In another example, angled ports 22 installed at or approximately at 90 degrees with respect the horizontal axis of the bottom surface of the Petri dish 1 may obstruct microscopic viewing of a Petri dish bioreactor 100 and make it difficult to access the center of the Petri dish 1. Many microscopes and other viewing instruments have a limited space between the condenser and sample (short working distance). Microscope stages have plenty of space to support larger diameter dishes. High port angles (e.g., greater than 65 degrees) with respect to horizontal may be too tall and not fit into the microscope stage between the objective and condenser. Also, at these high angles, the ports and its connectors operatively connected to an adapter body 2 may interfere with light entering a light transmission window 23. In some embodiments, the ports can be movable such as pivotable between a working range (e.g., adjustable between a minimal or maximal angle, or between about 15 degrees and about 65 degrees, or other angles as disclosed herein). However, in some embodiments, angled ports 22 may be at any angle to the horizontal axis of the bottom surface of the culture plate including from about 0 degrees to about 90 degrees.

Figure 31A:
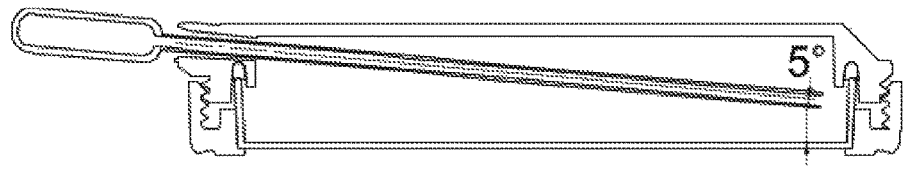
FIGS. 31A-31C is a diagram showing port angular positions at 5, 10, and 15 degrees and corresponding pipette locations in a bioreactor.
Figure 31B:
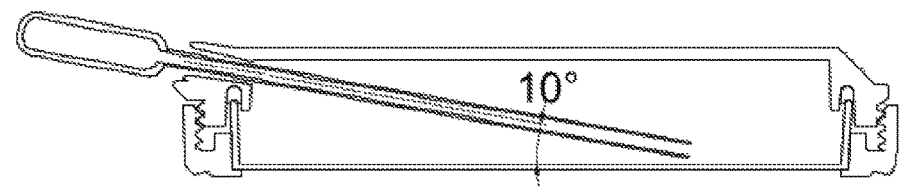
Figure 31C:
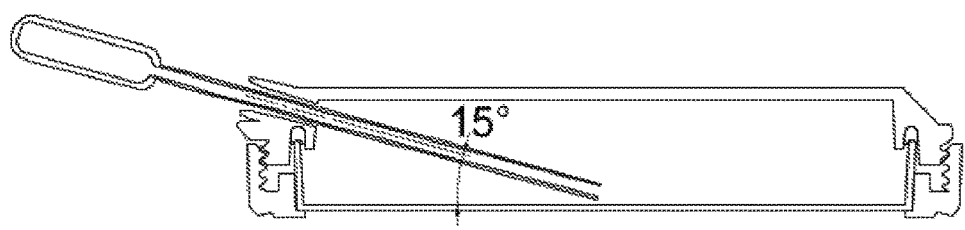
Figure 32:
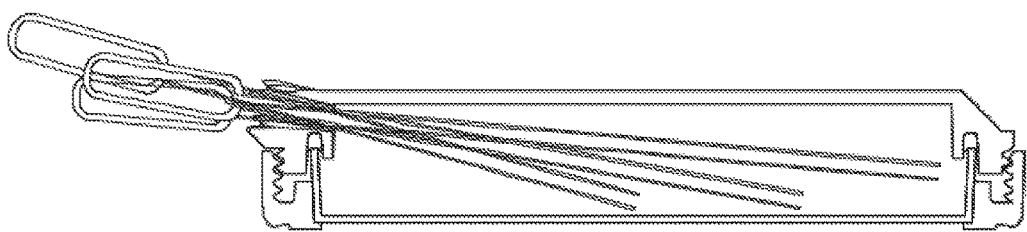
FIG. 32 is a diagram showing port angular positions at 5, 10, and 15 degrees and corresponding pipette locations in a bioreactor.
Figure 33:
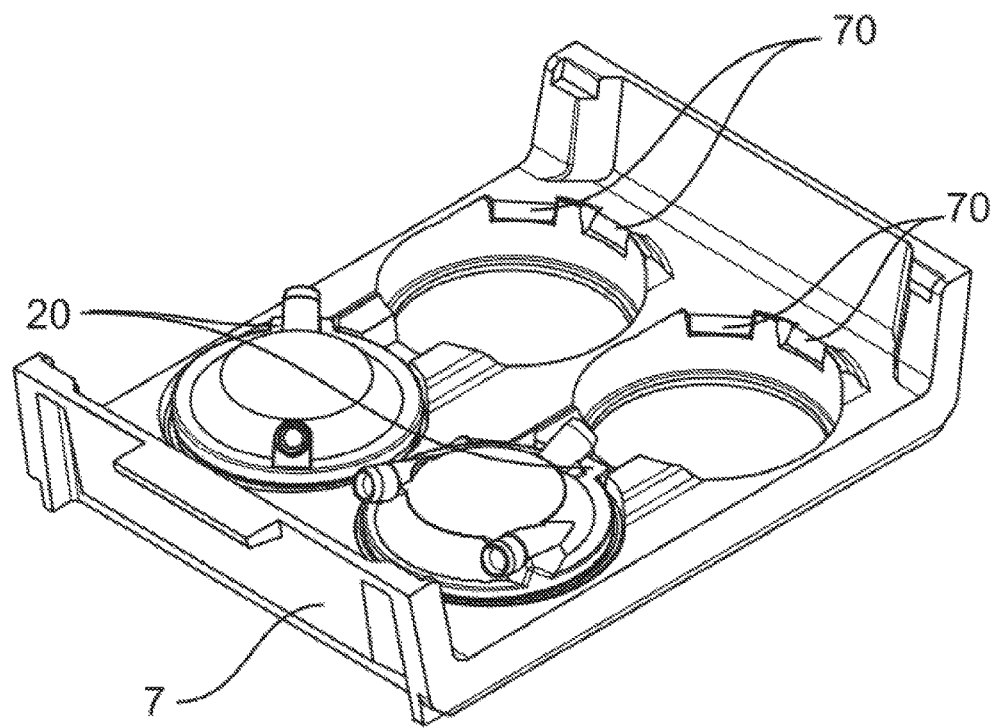
FIG. 33 is a diagram showing Petri dish bioreactors slotted into a four-position manifold.

In some embodiments, adapter body angled port angle 922 may be adjusted to accommodate a change in diameter of a Petri dish 1 used for a Petri dish bioreactor 100. As shown in an example embodiment shown in FIGS. 29A, 29B, 29C, 29D, 29E, 30A, 30B, 30C, and 30D, adapter body angled port angle 922 between about 35 and about 45 degrees can allow a transfer pipette 5 to access the center of a Petri dish 1 while not obstructing with light transmission or microscopic viewing. However, depending on a diameter of the Petri dish 1, the adapter body angled port angle 922 may be adjusted to allow the transfer pipette 5 to access to the center of the Petri dish 1. For example, as shown in FIGS. 31A, 31B, and 31C, an adapter body angled port angle 922 approximately at 15 degrees allows the transfer pipette 5 to access the center of the Petri dish 1 without obstructing light transmission or microscopic viewing. As diameter of the Petri dish 1 becomes smaller, adapter body angled port angle 922 may become larger to provide access to the center of the Petri dish 1 without obstructing light transmission or microscopic viewing. Likewise, as diameter of the Petri dish 1 becomes larger, adapter body angled port angle 922 may become smaller to provide access to the center of the Petri dish 1 without obstructing light transmission or microscopic viewing. FIG. 32 is an overlaid illustration of the transfer pipette 5 inserted into a Petri dish bioreactor 100 through an angled port 22 at 5, 10, and 15 degrees.

A gasket 3 may be made out of a deformable material such as, for example, silicone, natural rubber, neoprene, or polytetrafluoroethylene. The gasket 3 may be heat resistant for an autoclavable version. The gasket 3 may have a circular or other shape to conform with the sidewall geometry of the culture plate, and its dimension may vary corresponding to size of a Petri dish 1 used within a Petri dish bioreactor 100. In some embodiments, the gasket 3 may have circular, semicircular, or flat cross sections, as shown in FIG. 26. The gasket 3 may be manufactured with, for example, injection molding, extrusion, or sheet cutting. In some embodiments, the Petri dish bioreactor 100 does not include the gasket 3 and the compression between the adapter body 2 and Petri dish 1 is sufficient to create a watertight and airtight seal.

In some embodiments, the adapter body 2 has at least one, two, or more indexing extrusions 20 on its outer contour to prevent rotation and allow for indexing when inserted into a carrier, storage device, or microscope stage adapter. The indexing extrusion 20 may be rectangular in shape or in any other shape sufficient to prevent rotation and allow for indexing. In some embodiments, the adapter body 2 has two indexing extrusions 20 placed on opposite sides of the adapter body 2. In some embodiments, the adapter body 2 has four indexing extrusions 20 evenly or unevenly spaced from each other.

In some embodiments, the Petri dish 1, that is held by a internally threaded compression cap, telescopes entirely within an externally threaded adapter providing a reduced risk of environmental contamination if the dish overflows. A containment moat 43 of the adapter compression cap 4 can capture liquid overflow from the Petri dish 1.

In some embodiments, the adapter compression cap 4 is shaped like a compression nut with a substantially circular window that allows for unobstructed viewing through the Petri dish 1. The adapter compression cap 4 may be manufactured with materials that are amenable to injection molding, 3D punting, or CNC milling. It can be made from a thermoplastic that is fatigue resistant and heat resistant for versions that are autoclavable. The adapter compression cap material can allow for repeatable and efficient compression of the Petri dish 1 against the gasket 3 to achieve and maintain a watertight and airtight seal. This plastic may be a material such as polysulfone, acetal, or polycarbonate. In the threaded version, the adapter compression cap 4 screws into the adapter body 2. In some embodiments, the connector, e.g., threads can be external to, and spaced apart from the interior surface of the petri dish bioreactor which can advantageously decrease the risk of contamination in some cases.

In an aspect of the invention, the adapter body 2 and the adapter compression cap 4 are manufactured with materials that are amenable to injection molding, 3D printing, or CNC milling. They are made out of a durable optically clear and biologically compatible material such as polysulfone, polycarbonate, or polystyrene. The material can be non-deforming, fatigue resistant, biocompatible, chemically inert, and transparent. Autoclavable versions can be made from materials that include the property of high heat resistance.

In some embodiments, a Petri dish bioreactor 100 can include one or more baffles 6 to change a fluid flow profile 61. The baffles 6 can be removable or integrated into an adapter body 2 of the Petri dish bioreactor 100. Use of one or more baffles 6 allow a controlled distribution of solution to the bulk of the cells at the bottom of the Petri dish. This solution can provide nutrients or apply medication to specific regions of the bioreactor. The baffle 6 can be semilunar or circular shaped as to not interfere with light transmission or microscopic viewing. A baffle 6 is a plastic or elastomeric cylinder with cut outs that partition the internal volume of the Petri dish bioreactor into interconnected compartments with designated fluid pathways. The cut out height dimensions can be, e.g., from 1 mm to about 12 mm or at about 1 mm, 2 mm, 4 mm, 6 mm, 8 mm, 10 mm or 12 mm and ranges including any two of the aforementioned values. The cut outs can be semicircular, semi ovoid, square, rectangular or trapezoidal in shape. These cut outs align with the internal openings of various entry and exit ports allowing for a predetermined directional fluid flow through the Petri dish bioreactor. When the baffle 6 can include a flexible or semi rigid material, the directional flow can have less to no side leakage between compartments due to compression of the baffle 6 against an inner surface of a wall defining an adapter body gasket groove 27.

Figure 35:
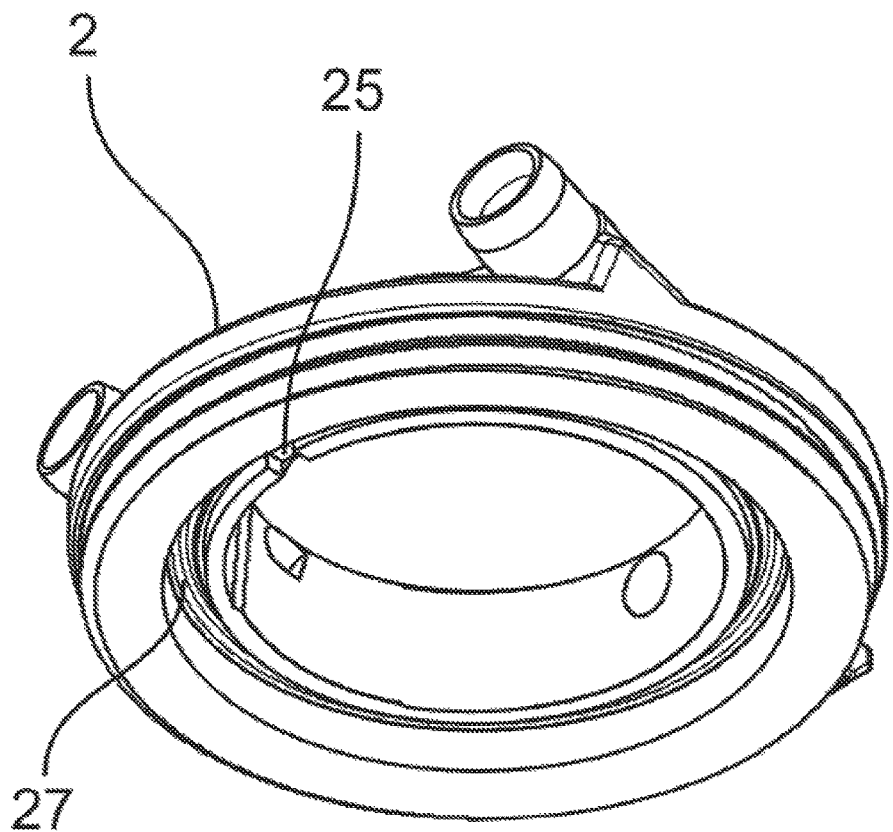
FIG. 35 is a diagram showing an adapter body with an indexing slot for baffle alignment.

FIG. 35 is an illustration showing a perspective view of an adapter body 2 from below. The adapter body 2 can have at least one baffle indexing slot 25 which is formed on an annular ridge that defines a gasket groove 27 for the adapter body 2.

Figure 36:
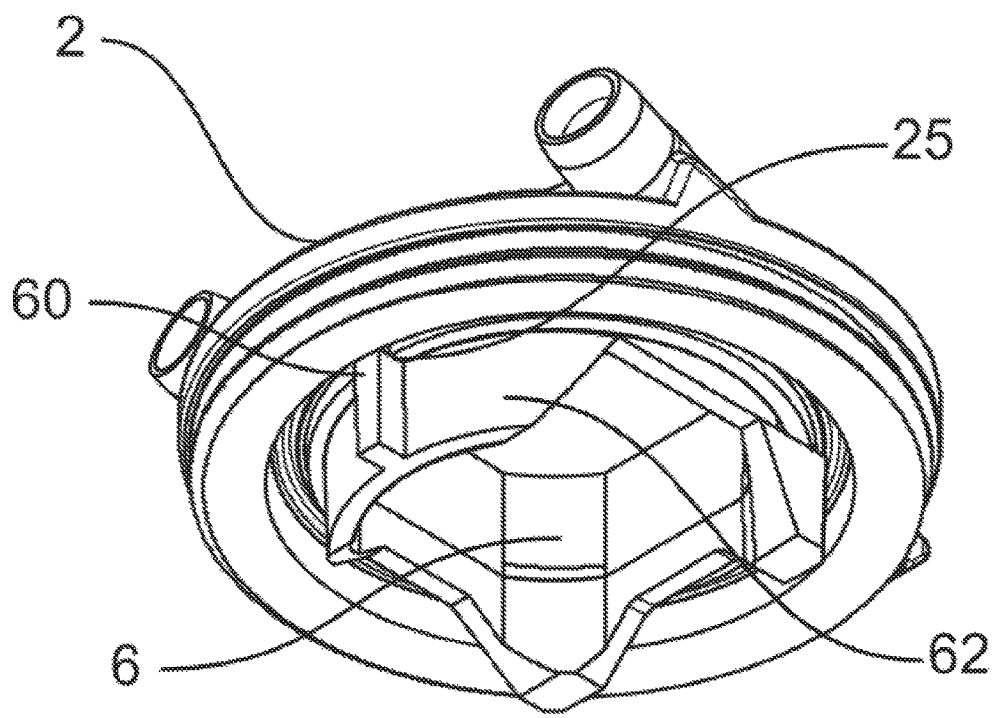
FIG. 36 is a diagram showing an adapter body incorporated with a baffle.

FIG. 36 is an illustration showing a perspective view of an adapter body 2 with a baffle 6 installed. In some embodiments, the baffle 6 is made out of the same material as the adapter body 2. In other embodiments, the baffle 6 is made of a material that is different from the adapter body 2. The Petri dish baffle 6 can be either removable or non-removably affixed to the Petri dish, and made from, for example, biocompatible rigid, semi rigid, or flexible plastics or elastomer such as polysulfone, PTCG, polystyrene, or silicone. In some embodiments, the baffle 6 includes a baffle indexing extrusion 60 that mates with the adapter body baffle indexing slot 25, and at least one flow barrier 62 extending from the adapter body 2 towards the adapter compression cap 4. The at least one flow barrier 62 of the baffle 6 may be vertical with respect to the adapter body 2. In some embodiments, the at least one flow barrier 62 of the baffle 6 may not be vertical with respect to the adapter body 2. The adapter body baffle indexing slot 25 of the adapter body 2 and the baffle indexing extrusion 60 of the baffle 6 interact so that the baffle 6 may be fixedly and removably attached to the adapter body 2. In some embodiments, there may be more than one adapter body baffle indexing slot 25 and the baffle 6 may have more than one baffle indexing extrusion 60.

The adapter body baffle indexing slot 25 may be radially movable with respect to the center of the adapter body 2. In other embodiments, the adapter body baffle indexing slot 25 is in a fixed location so that the location of the baffle 6 is fixed with respect to the adapter body 2. Various methods may be utilized to keep the baffle 6 operatively connected to the adapter body 2. For example, a friction-fit method may be used to keep the baffle 6 fixedly attached to the adapter body 2.

Figure 37:
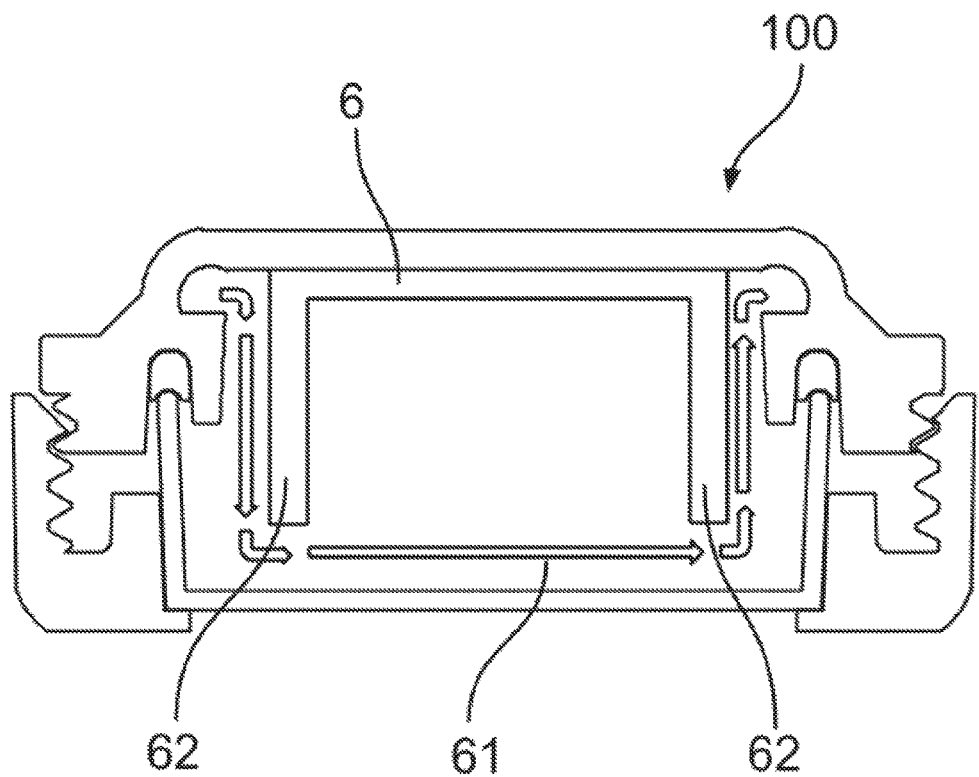
FIG. 37 is a cross-sectional diagram showing an altered flow profile through a Petri dish bioreactor with a baffle.
Figure 38:
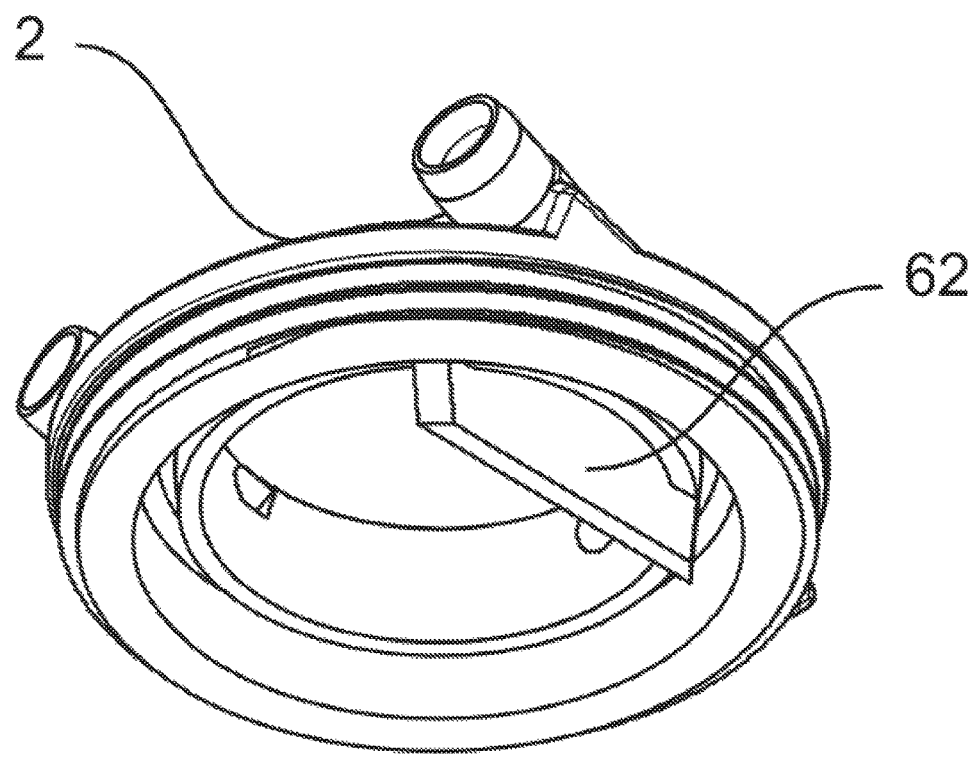
FIG. 38 is a diagram showing an integrated adapter body baffle with one flow barrier.
Figure 39:
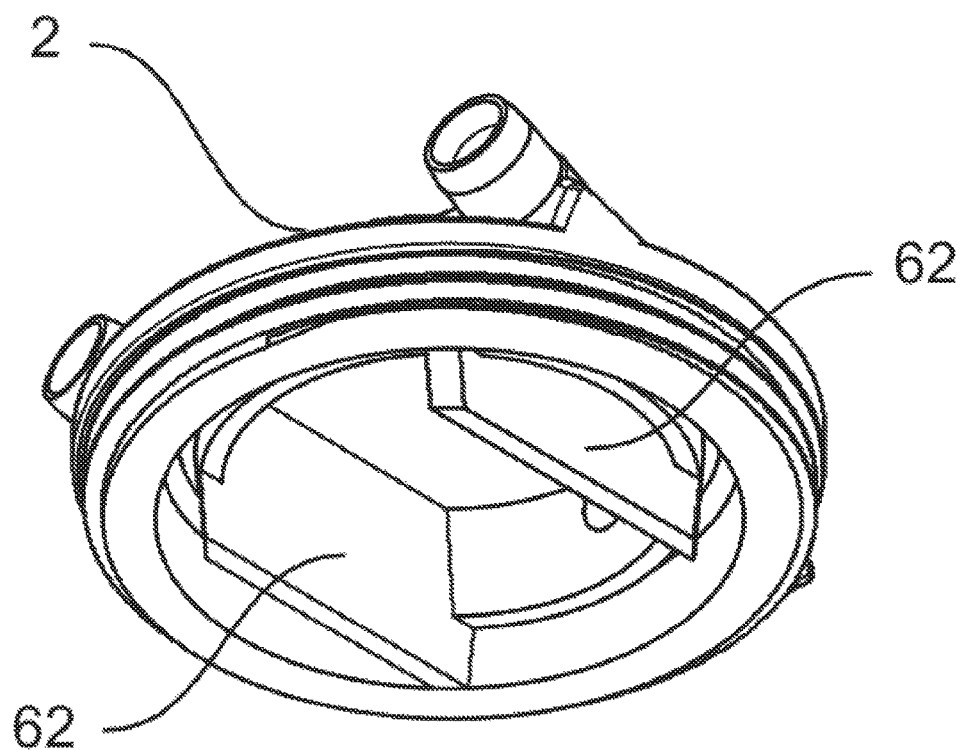
FIG. 39 is a diagram showing an integrated adapter body baffle with two flow barriers.

FIG. 37 shows a cross section of the Petri dish bioreactor 100 with a baffle 6 installed. As shown in FIG. 37, the baffle 6 includes at least one flow barrier 62 that can alter the flow profile 61 of the Petri dish bioreactor 100. In some embodiments, a flow barrier 62 may be integrated into an adapter body 2. FIG. 38 shows an adapter body 2 integrated with one flow barrier 62. FIG. 39 shows an adapter body 2 integrated with two flow barriers 62.

The Petri dish bioreactor 100 may be connected to a fluid handling system as shown, for example, in FIG. 8. Various types of tubes may be coupled to the adapter body ports 22 to allow perfusion within the bioreactor. In addition, perfusion through two, three, or more Petri dish bioreactors 100 can be achieved by connecting the inlet and outlet ports of multiple Petri dish bioreactors daisy chained or isolated depending on the application. FIG. 22 shows a multiplexed embodiment of coupled Petri dish bioreactors. A perfusion pump such as a peristaltic pump or syringe pump can be used for infusion through one or more Petri dish bioreactors 100.

In some embodiments, the Petri dish bioreactor 100 is mounted on a custom microscope stage adapter and is monitored using a microscope. In some embodiments, the Petri dish bioreactor is monitored using cameras mounted into custom holders. Macroscopic or microscopic cameras can be positioned above or below to monitor intermittently or continuously events within the Petri dish bioreactor Multiple Petri dish bioreactors can be placed into a manifold for transport and installation into a microscopic viewing device for high throughput applications.

Figure 34:
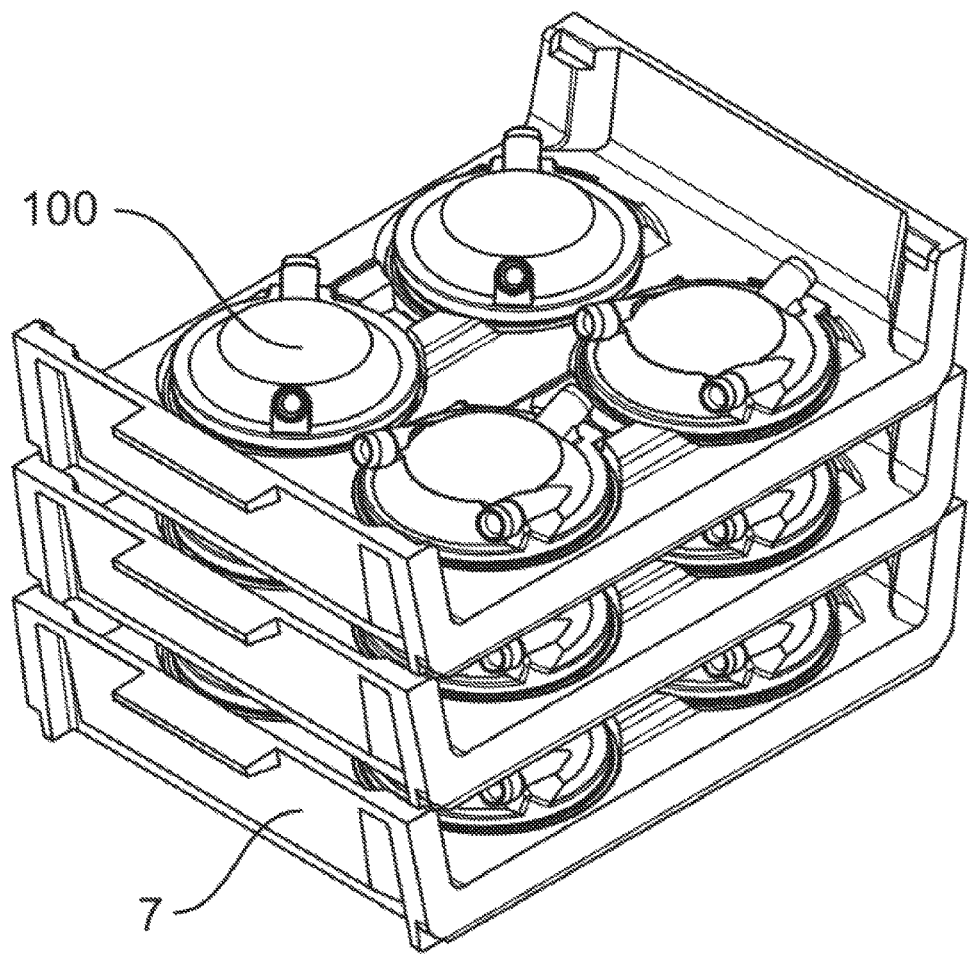
FIG. 34 is a diagram showing Petri dish bioreactors placed on storage carriers stacked for storage.

The Petri dish bioreactors 100 can also be stored in storage carriers 7 as shown in FIG. 34 which can be configured for modular, e.g., vertical stacking. The storage carriers 7 are then placed into an incubator that provides temperature and $CO_2$ control, and/or other parameters. Each storage manifold 7 has an area for sample identification and at least one, two, or more storage manifold indexing slots 70. The at least one storage manifold indexing slot 70 can be configured to mate with at least one, two, or more indexing tabs, e.g., extrusion 20 to register the Petri dish bioreactors 100 to accurate and repeatable positions relative to the storage manifold 7 attached to a microscope stage. In some embodiments, the indexing tabs 20 result in the Petri dish bioreactor's circumferential perimeter not being a perfect circle in some cases. If multiple slots 70 and tabs 20 are present, they can be asymmetrically spaced apart as shown, or symmetric in other embodiments. On automated microscope systems, this indexing system allows a user to easily find microscopic positions on the Petri dish bioreactors 100 after they are removed from and/or placed into the storage manifold 7, and identify individual Petri dish bioreactors 100 in some cases. In some embodiments, the storage carriers 7 may be stackable.

The sample, including cells, drugs, and/or other agents can be directly placed into the Petri dish prior to the Petri dish bioreactor assembly. Post-assembly, cells or drugs can be directly injected through the port with a small gauge needle or via barbed, Luer, or other connection. Needleless connections or diaphragms are other examples of options.

The Petri dish bioreactor 100 can be used for the cultivation and microscopic observation of cells. Microbiologic applications for the device include but are not limited to microbiome modeling, microbiome clonal expansion, microbiome repository, and observable antibiotic sensitivity testing. Cell culture for tissue engineering, pathology modeling, and ex vivo drug testing are other potential uses. Cross contamination of potential human pathogens can be of high importance in a clinical and laboratory setting so this device provides a platform for the transport, storage, sterile cultivation, observation, and controlled manipulation of cells. In some embodiments, environment inside a Petri dish bioreactor 100 is controlled, wherein the internal temperature of the bioreactor is controlled by heaters and a controller system, wherein the extracellular pH is controlled using a chemical buffer such as HEPES (4-(2-hydroxyethyl)-1-piperazineethanesulfonic acid) or MOPS (3-(N-morpholino) propanesulfonic acid), wherein the internal bioreactor pH is controlled using a bicarbonate buffer with a set atmospheric carbon dioxide level, and wherein the internal bioreactor pH is controlled using a bicarbonate buffer with a media carbonator.

The Petri dish bioreactor 100 can be disposed of in cases of highly pathogenic contamination. Cold sterilization and autoclaving the Petri dish bioreactor is an option. Attempts to remove biofilm with a scrubber and brushes prior to sterilization can be recommended in some cases.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above.

Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "accessing a bioreactor via a pipette" includes "instructing the accessing of a bioreactor via a pipette."

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An isolated bioreactor system for creating a watertight and airtight seal between the bioreactor system and a surrounding environment, the system comprising:
   an adapter compression cap, operatively connected to a petri dish and configured to hold the petri dish in place, wherein the adapter compression cap comprises a first connection component;
   an adapter body comprising:
      a transmission window configured to allow transmission of light and unobstructed viewing through a top surface of the adapter body to the petri dish;
      at least one port comprising an external end, an internal end, and a conduit therebetween, the internal end of the at least one port comprising a surface directly attached to an upper surface of the adapter body, the at least one port at an angle with respect to a horizontal axis defined by a bottom surface of the petri dish, the angle sufficient to permit access to a bottom of the petri dish, wherein the angle is between about 15 degrees and about 65 degrees; and a second connection component that interacts with the first component to generate compression between the adapter body and the adapter compression cap; and a gasket operatively connected to the adapter body and the petri dish, wherein the gasket comprises at least one arcuate concave groove that, when compressed against the petri dish, interacts with a wall of the petri dish.

2. The system of claim 1, comprising at least two ports.

3. The system of claim 2, wherein the at least two ports are at an angle with respect to a horizontal axis of an inferior surface of the petri dish, wherein the angle is between about 15 degrees and about 65 degrees.

4. The system of claim 3, wherein the at least two ports are hingedly connected to the adapter body.

5. The system of claim 4, wherein the angle may be adjusted between about 15 degrees and about 65 degrees.

6. The system of claim 1, wherein the first connection component of the adapter compression cap and the second connection component of the adapter body comprise complementary threaded surfaces.

7. The system of claim 1, further comprising an environment sensor, wherein the environment sensor is in communication with one or more of the at least one port.

8. The system of claim 1, wherein the at least one port is operably connected to a fluid or gas pump.

9. The system of claim 1, wherein the adapter body comprises a baffle.

10. The system of claim 9, wherein the baffle comprises at least one barrier wall to alter natural flow within the bioreactor system.

11. A bioreactor system with an enhanced seal, comprising:

a culture plate comprising a sidewall, a closed inferior end, and an open superior end;

a first adapter component, the first adapter component comprising a central aperture configured to house the culture plate therein, the first adapter component further comprising an inner ring defining the central aperture, the inner ring configured to contact the sidewall of the culture plate, and the first adapter component further comprising an outer ring comprising a reversible locking element;

an arcuate gasket comprising a superior-facing surface, an inferior-facing surface, and lateral surfaces, the inferior-facing surface comprising a preformed concave groove configured to mate with a top peripheral edge of the sidewall of the culture plate within the groove, the superior-facing surface defined by an arcuate shape and located at an opposite side of the arcuate gasket in relation to the inferior-facing surface; and a second adapter component comprising a reversible locking element, at least one port, and an annular ridge defining a circumferential gasket groove, the circumferential groove defining a slot configured to fit the arcuate gasket therein, wherein the bioreactor system is reversibly transformable from an unlocked configuration to a locked configuration, such that an airtight seal within the culture plate is created in the locked configuration.

12. The bioreactor system of claim 11, wherein the second adapter component comprises at least one laterally-extending tab.

13. The bioreactor system of claim 11, wherein the at least one port of the second adapter component is at an angle with respect to a horizontal axis of an inferior surface of the culture plate, wherein the angle is between about 15 degrees and about 65 degrees.

14. The bioreactor system of claim 11, further comprising at least one baffle configured to separate adjacent zones of the culture plate, wherein the at least one baffle is configured to fit within a slot of the second adapter component.

15. The bioreactor system of claim 11, wherein the reversible locking element of the first adapter component and the second adapter component comprise complementary threaded surfaces.

16. The bioreactor system of claim 11, wherein the culture plate is removably attached to the first adapter component.

17. The bioreactor system of claim 11, wherein the culture plate is integrally formed with the first adapter component.

18. The bioreactor system of claim 11, wherein the arcuate gasket comprises a flexible material.

19. An isolated bioreactor system for creating a watertight and airtight seal between the bioreactor system and a surrounding environment, the system comprising:

an adapter compression cap, operatively connected to a petri dish and configured to hold the petri dish in place, wherein the adapter compression cap comprises a first connection component;

an adapter body comprising:

a transmission window configured to allow transmission of light and unobstructed viewing through a top surface of the adapter body to the petri dish;

at least two ports comprising an external end, an internal end, and a conduit therebetween, the internal end of the at least two ports comprising a surface directly attached to an upper surface of the adapter body, the at least two ports at an angle with respect to a horizontal axis defined by a bottom surface of the petri dish, the angle sufficient to permit access to a bottom of the petri dish, wherein the angle is between about 15 degrees and about 65 degrees; and a second connection component that interacts with the first component to generate compression between the adapter body and the adapter compression cap; and a gasket operatively connected to the adapter body and the petri dish, wherein the at least two ports are at an angle with respect to a horizontal axis of an inferior surface of the petri dish, wherein the angle is between about 15 degrees and about 65 degrees; and wherein the at least two ports are hingedly connected to the adapter body.

20. The system of claim 19, wherein the angle may be adjusted between about 15 degrees and about 65 degrees.

21. The system of claim 19, wherein the first connection component of the adapter compression cap and the second connection component of the adapter body comprise complementary threaded surfaces.

22. The system of claim 19, wherein the gasket comprises at least one arcuate concave groove that, when compressed against the petri dish, interacts with a wall of the petri dish.

23. The system of claim 19, further comprising an environment sensor, wherein the environment sensor is in communication with one or more of the at least one port.

24. The system of claim 19, wherein the at least one port is operably connected to a fluid or gas pump.

25. The system of claim 19, wherein the adapter body comprises a baffle.

26. The system of claim 25, wherein the baffle comprises at least one barrier wall to alter natural flow within the bioreactor system.

\* \* \* \* \*